US012629006B2

(12) United States Patent
Chu

(10) Patent No.: US 12,629,006 B2
(45) Date of Patent: May 19, 2026

(54) ENDOSCOPE HANDLE AND DEPLOYMENT DEVICE

(71) Applicant: BOSTON SCIENTIFIC SCIMED, INC., Maple Grove, MN (US)

(72) Inventor: Michael S. H. Chu, Brookline, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 908 days.

(21) Appl. No.: 17/698,548

(22) Filed: Mar. 18, 2022

(65) Prior Publication Data

US 2022/0304548 A1     Sep. 29, 2022

Related U.S. Application Data

(60) Provisional application No. 63/165,356, filed on Mar. 24, 2021.

(51) Int. Cl.
  *A61B 1/005*      (2006.01)
  *A61B 1/00*       (2006.01)
  *A61B 1/018*      (2006.01)
(52) U.S. Cl.
  CPC ........ *A61B 1/0052* (2013.01); *A61B 1/00087* (2013.01); *A61B 1/0011* (2013.01); *A61B 1/0057* (2013.01); *A61B 1/018* (2013.01)
(58) Field of Classification Search
  CPC ... A61B 1/307; A61B 1/0052; A61B 1/00087; A61B 1/0011; A61B 1/0057;
  (Continued)

(56) References Cited

U.S. PATENT DOCUMENTS 7,789,825 B2    9/2010  Nobis et al.
8,007,432 B2    8/2011  Vakharia et al.
(Continued)

FOREIGN PATENT DOCUMENTS

JP        1993015484        1/1993
JP        2007151595 A      6/2007
(Continued)

OTHER PUBLICATIONS

Boston Scientific, Lithovue Empower™, Retrieval Deployment Device, Brochure, URO-554-002-AA, 4 pages, Jul. 2018.
(Continued)

*Primary Examiner* — Anh Tuan T Nguyen
*Assistant Examiner* — Li-Ting Song
(74) *Attorney, Agent, or Firm* — Seager, Tufte & Wickhem, LLP

(57)                    ABSTRACT
A medical device configured to be actuated using a first hand may include a handle comprising a proximal handle portion and a distal handle portion, an elongate shaft extending distally from the distal handle portion, wherein the elongate shaft includes a distal tip that is deflectable using a first actuation mechanism secured to the proximal handle portion, wherein the handle includes a port in communication with the elongate shaft, and an actuatable medical instrument configured to be slidably disposed within the elongate shaft and the port. A proximal end of the actuatable medical instrument may be operably connected to a second actuation mechanism secured to the proximal handle portion. The first actuation mechanism may be configured to be actuated by a thumb of the first hand. The second actuation mechanism may be configured to be actuated by the thumb of the first hand.

18 Claims, 18 Drawing Sheets

(58) Field of Classification Search

CPC ..... A61B 1/018; A61B 1/00066; A61B 1/009; A61B 1/005; A61B 1/0051; A61B 1/00098; A61B 1/00133

See application file for complete search history.

(56) References Cited

U.S. PATENT DOCUMENTS

| | | | |
|---|---|---|---|
| 9,095,686 B2 | 8/2015 | Zanne et al. | |
| 9,433,340 B2 | 9/2016 | Jones et al. | |
| 10,667,673 B2 | 6/2020 | Su et al. | |
| 10,881,832 B2 | 1/2021 | Chu | |
| 2007/0225754 A1 | 9/2007 | Measamer et al. | |
| 2008/0300462 A1* | 12/2008 | Intoccia | A61B 1/0055 600/146 |
| 2010/0004591 A1* | 1/2010 | Barenboym | A61B 1/00042 604/95.04 |
| 2010/0004633 A1* | 1/2010 | Rothe | A61B 1/0051 604/528 |
| 2011/0208002 A1* | 8/2011 | Kishioka | A61B 1/00052 600/146 |
| 2013/0144125 A1* | 6/2013 | Konstorum | A61B 1/0057 600/150 |
| 2013/0190561 A1* | 7/2013 | Oskin | A61B 1/005 600/110 |
| 2014/0088497 A1* | 3/2014 | Campbell | A61B 1/0052 604/95.04 |
| 2014/0251042 A1* | 9/2014 | Asselin | F16H 21/40 74/89 |
| 2014/0275763 A1 | 9/2014 | King et al. | |
| 2014/0316203 A1* | 10/2014 | Carroux | A61B 1/00133 600/146 |
| 2014/0358028 A1* | 12/2014 | Vetter | A61B 10/0266 600/567 |
| 2016/0089127 A1* | 3/2016 | Kirkemo | A61B 1/0052 606/110 |
| 2016/0213387 A1* | 7/2016 | DeGraaf | A61B 17/221 |
| 2017/0143195 A1 | 5/2017 | Yee et al. | |
| 2017/0325660 A1* | 11/2017 | Wang | A61B 1/0052 |
| 2018/0117280 A1* | 5/2018 | Chu | A61B 1/0051 |
| 2019/0008363 A1* | 1/2019 | Walish | A61B 1/018 |
| 2019/0021707 A1 | 1/2019 | Belsky et al. | |
| 2019/0029498 A1 | 1/2019 | Mankowski et al. | |
| 2019/0083116 A1* | 3/2019 | Mansfield | A61B 17/00234 |
| 2019/0133564 A1* | 5/2019 | Kirkemo | A61B 1/0055 |
| 2019/0350440 A1* | 11/2019 | Leong | A61B 1/0052 |
| 2020/0077880 A1* | 3/2020 | Ouyang | A61B 1/0057 |
| 2020/0196834 A1 | 6/2020 | Tah | |
| 2020/0337526 A1* | 10/2020 | Chu | A61B 1/00094 |
| 2021/0007582 A1* | 1/2021 | Graveley | A61B 1/00098 |
| 2021/0085153 A1* | 3/2021 | Chu | A61B 1/0014 |
| 2021/0161555 A1* | 6/2021 | Winegar | A61B 1/0058 |
| 2021/0353132 A1* | 11/2021 | Gorringe | A61B 1/0052 |
| 2021/0386441 A1* | 12/2021 | Heimberger | A61B 1/00066 |
| 2023/0157523 A1* | 5/2023 | Teatini | A61B 1/00098 600/107 |
| 2023/0172433 A1* | 6/2023 | Levinson | A61B 1/00066 600/109 |
| 2023/0172439 A1* | 6/2023 | Lund | A61B 1/00042 600/148 |
| 2023/0404366 A1* | 12/2023 | Wilder | A61B 1/0058 |
| 2025/0098953 A1* | 3/2025 | Wolfe | A61B 1/00066 |
| 2025/0235089 A1* | 7/2025 | Kaneta | A61B 1/00103 |

FOREIGN PATENT DOCUMENTS

| | | |
|---|---|---|
| JP | 2013248118 A | 12/2013 |
| WO | 2014103829 A1 | 3/2014 |
| WO | 2020160522 A1 | 8/2020 |

OTHER PUBLICATIONS

International Search Report and Written Opinion dated Jun. 1, 2022 for International Application No. PCT/US2022/020951.

* cited by examiner

DETAIL A

DETAIL B

DETAIL C

DETAIL D

DETAIL C

DETAIL B

DETAIL A

DETAIL D

ENDOSCOPE HANDLE AND DEPLOYMENT DEVICE

CROSS REFERENCE TO RELATED APPLICATIONS

This application claims the benefit of and priority to U.S. Provisional Patent Application Ser. No. 63/165,356 filed on Mar. 24, 2021, the disclosure of which is incorporated herein by reference.

TECHNICAL FIELD

The present disclosure pertains to medical devices and systems and methods for manufacturing and using medical devices and systems. More particularly, the present disclosure pertains to endoscopes, components thereof, and methods of manufacturing and using endoscopes.

BACKGROUND

Endoscopes are used during medical procedures for diagnostic and therapeutic purposes. For instance, flexible ureteroscopes are utilized in the examination and treatment of kidneys and may generally include features which improve treatment site accessibility and patient comfort. Flexible endoscopes, including ureteroscopes, may be provided with a flexible tip section that is controlled by a physician via manipulation of various components attached to the scope's handle. Such manipulation enables the physician to maneuver the tip of the scope to different locations within the body (e.g., different locations within the kidney). Additionally, endoscopes, such as ureteroscopes and other endoscopic devices, are typically used in conjunction with other medical devices during a medical procedure. For example, urologists may use a flexible ureteroscope in combination with both a laser fiber and a retrieval device (e.g., retrieval basket) to pulverize kidney stones and/or to remove debris from the body. Accordingly, these procedures may require not only manipulating various features of the endoscope to control the tip of the scope, but also to introduce and manipulate ancillary devices used in conjunction with the endoscope. Ergonomics of the device(s) may be of notable importance to the user(s). There is an ongoing need to provide alternative endoscopes and components thereof, as well as alternative methods for manufacturing and using such endoscopic devices.

BRIEF SUMMARY

The disclosure provides design, material, manufacturing method and use alternatives for medical devices.

An example is an endoscope configured to be actuated using a first hand of a user. The endoscope includes a handle comprising a proximal handle portion and a distal handle portion. An elongate shaft extends distally from the distal handle portion. The elongate shaft includes a distal tip that is deflectable using a first actuation mechanism secured to the proximal handle portion. The handle includes a port in communication with the elongate shaft. An actuatable medical instrument is also provided and configured to be slidably disposed within the elongate shaft and the port. A proximal end of the actuatable medical instrument is operably connected to a second actuation mechanism secured to the proximal handle portion. The first actuation mechanism is configured to be actuated by a thumb of the first hand. The second actuation mechanism is configured to be actuated by the thumb of the first hand.

Alternatively or additionally to any of the embodiments above, the first actuation mechanism is self-locking.

Alternatively or additionally to any of the embodiments above, the first actuation mechanism includes a first hinged arm, a first biasing element, and a first tooth formed in the first hinged arm, the first tooth being configured to releasably engage a first plurality of teeth formed in the proximal handle portion.

Alternatively or additionally to any of the embodiments above, first actuation mechanism includes a first gear slidably disposed on the elongate shaft within the proximal handle portion and a second gear disposed within the proximal handle portion and operably connected to the first gear. The first gear is operably connected to the distal tip and the second gear is operably connected to the first hinged arm.

Alternatively or additionally to any of the embodiments above, rotational movement of the first hinged arm by the thumb of the first hand causes the first gear to axially translate along the elongate shaft;

wherein axial translation of the first gear causes deflection of the distal tip.

Alternatively or additionally to any of the embodiments above, the elongate shaft is rotatable relative to the proximal handle portion.

Alternatively or additionally to any of the embodiments above, the second actuation mechanism includes an actuation housing comprising a base portion and a cover portion configured to rotate relative to the base portion.

Alternatively or additionally to any of the embodiments above, the second actuation mechanism is self-locking.

Alternatively or additionally to any of the embodiments above, the second actuation mechanism includes a second hinged arm, a second biasing element, and a second tooth formed in the second hinged arm, the second booth being configured to releasably engage a second plurality of teeth formed in the actuation housing.

Alternatively or additionally to any of the embodiments above, the actuatable medical instrument includes an outer sheath having an annular strain relief disposed about a proximal end of the outer sheath and an inner wire slidably disposed within the outer sheath.

Alternatively or additionally to any of the embodiments above, the annular strain relief is fixedly attached to the base portion of the actuation housing and the inner wire is attached to the cover portion.

Alternatively or additionally to any of the embodiments above, the outer sheath is fixedly attached to the base portion of the actuation housing.

Alternatively or additionally to any of the embodiments above, the outer sheath is axially movable within the annular strain relief.

Alternatively or additionally to any of the embodiments above, the base portion includes a mounting slot configured to receive the proximal end of the outer sheath. The outer sheath includes a stop fixed at the proximal end of the outer sheath. The second actuation mechanism includes a compression spring disposed within the mounting slot and configured to bias the outer sheath toward a distal end of the mounting slot.

Alternatively or additionally to any of the embodiments above, the actuation housing is removably secured to proximal handle portion.

Another example is an endoscope configured to be actuated using a first hand of a user. The endoscope includes a handle comprising a proximal handle portion and a distal handle portion extending along a central longitudinal axis. An elongate shaft extends distally from the distal handle portion. The elongate shaft includes a distal tip that is deflectable using a first actuation mechanism secured to the proximal handle portion. The handle includes a port in communication with a lumen extending through the elongate shaft. The first actuation mechanism is configured to be actuated by the first hand in a first position relative to the handle. The first actuation mechanism includes a first hinged arm having a first free end and a first hinged end opposite the first free end, a first biasing element, and a first tooth formed in the first hinged end, the first tooth being configured to releasably engage a first plurality of teeth formed in the proximal handle portion. The first biasing element biases the first hinged arm toward a first locked position, wherein the first free end of the first hinged arm is biased away from the handle.

Alternatively or additionally to any of the embodiments above, the endoscope further includes an actuatable medical instrument configured to be slidably disposed within the lumen of the elongate shaft and the port. A proximal end of the actuatable medical instrument is operably connected to a second actuation mechanism configured to be secured to the proximal handle portion.

Alternatively or additionally to any of the embodiments above, the second actuation mechanism is configured to be actuated by the first hand in the first position relative to the handle.

Alternatively or additionally to any of the embodiments above, the second actuation mechanism includes a second hinged arm having a second free end and a second hinged end opposite the second free end, a second biasing element, and a second tooth formed in the second hinged end, the second tooth being configured to releasably engage a second plurality of teeth.

Alternatively or additionally to any of the embodiments above, the second biasing element biases the second hinged arm toward a second locked position, wherein the second free end of the second hinged arm is biased away from the handle.

Alternatively or additionally to any of the embodiments above, the second actuation mechanism includes an actuation housing comprising a base portion and a cover portion configured to rotate relative to the base portion.

Alternatively or additionally to any of the embodiments above, the proximal handle portion includes a deflection indicator disposed on an outside surface of the proximal handle portion. When the first hinged arm is moved away from a home position relative to the proximal handle portion the deflection indicator is visible.

Another example is an endoscope configured to be actuated using a first hand of a user. The endoscope includes a handle comprising a proximal handle portion and a distal handle portion detachably couplable to the proximal handle portion. The endoscope also includes an elongate shaft having a distal portion extending distally from the distal handle portion and a proximal portion extending proximally from the distal handle portion into the proximal handle portion. A first actuation mechanism is configured to deflect a distal tip of the elongate shaft. A first gear or linkage of the first actuation mechanism is coupled to the proximal portion of the elongate shaft and a second gear or linkage of the first actuation mechanism is coupled to the proximal handle portion. The first gear or linkage engages the second gear or linkage when the distal handle portion is coupled to the proximal handle portion.

Alternatively or additionally to any of the embodiments above, the distal handle portion and the elongate shaft are rotatably coupled to the proximal handle portion.

Alternatively or additionally to any of the embodiments above, the first gear or linkage is a worm gear longitudinally slidable along the proximal portion of the elongate shaft.

Alternatively or additionally to any of the embodiments above, the endoscope includes a plurality of pull wires extending from the worm gear to the distal tip.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description in connection with the accompanying drawings. It is noted that all figures are not necessarily drawn to scale and/or selected elements may change scale within the figure in order to facilitate a clear view of the elements and/or a clear understanding of the elements. Changes in scale will be apparent to the skilled artisan and need not be expressly identified.

Figure 1:
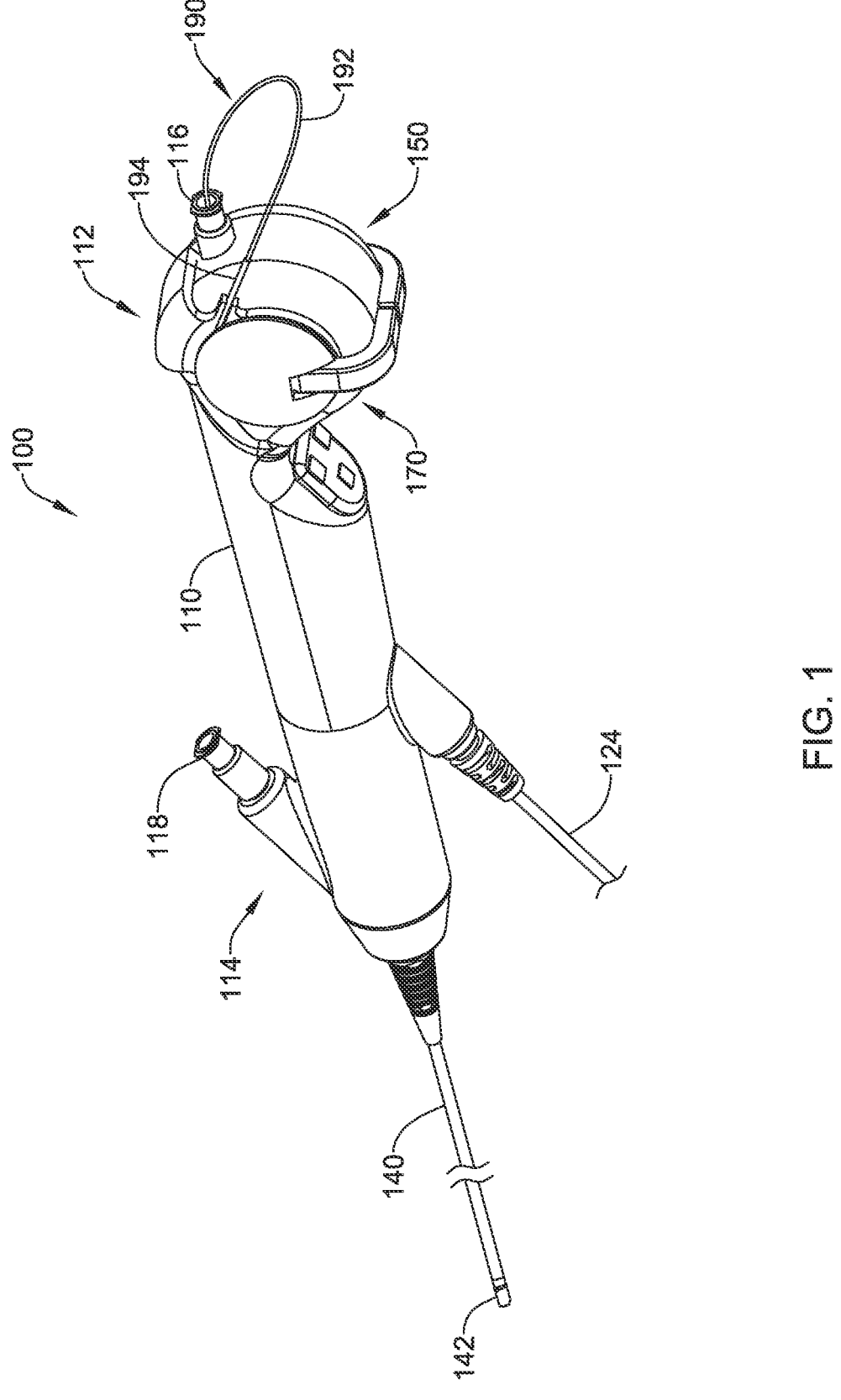
FIGS. 1-2 illustrate an example medical device.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the current disclosure. Those skilled in the art will recognize that the various elements described and/or shown may be arranged in various combinations and configurations without departing from the scope of the disclosure. The detailed description and drawings illustrate example embodiments of the current disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed example(s). Each instance of the features may include and/or be encompassed by the singular disclosure(s), unless expressly stated to the contrary. For simplicity and clarity purposes, not all elements of the current disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to implement the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The following figures illustrate selected components and/or arrangements of medical devices and/or systems and methods of using the same. It should be noted that in any given figure, some features may not be shown, or may be shown schematically, for simplicity. Additional details regarding some of the components of the implant and/or the system may be illustrated in other figures in greater detail. While discussed in the context of accessing and treating the urinary tract, the implant and/or the system may also be used for other interventions and/or percutaneous medical procedures within a patient. Similarly, the devices and methods described herein with respect to percutaneous deployment may be used in other types of surgical procedures, as appropriate. For example, in some examples, the devices may be used in a non-percutaneous procedure. Devices and methods in accordance with the disclosure may also be adapted and configured for other uses within the anatomy.

FIG. 1 illustrates selected aspects of a medical device (e.g., endoscope) 100. The medical device 100 may include a handle 110 comprising a proximal handle portion 112 and a distal handle portion 114 extending along a longitudinal axis. In some embodiments, the medical device 100 may include an elongate shaft 140 extending distally from the distal handle portion 114. The elongate shaft 140 may include a distal tip 142 that is deflectable using a first actuation mechanism 150 secured to the proximal handle portion 112. In some embodiments, the distal tip 142 may be deflectable within a deflection plane. In some embodiments, the distal tip 142 may be deflectable about plus or minus 90 degrees, about plus or minus 180 degrees, about plus or minus 270 degrees, about plus or minus 360 degrees, or another amount as desired.

In some embodiments, the elongate shaft 140 may have a length of about 26.5 inches (about 67.3 centimeters). In some embodiments, the elongate shaft 140 may have a length of about 15 inches (about 38.1 centimeters), about 20 inches (about 50.8 centimeters), about 25 inches (about 63.5 centimeters), about 28 inches (about 71.1 centimeters), about 30 inches (about 76.2 centimeters), about 35 inches (about 88.9 centimeters), etc. In general, the elongate shaft 140 may take the form of a polymer tube, or a rigid metal tube, in some instances. In some embodiments, the elongate shaft 140 may be constructed with a reinforcing braid, liner, web, weave, etc.

The elongate shaft 140 may include a lumen (e.g., a working channel) extending through the elongate shaft 140 from the handle 110 to the distal tip 142. In some embodiments, the proximal handle portion 112 may include a proximal port 116 in communication with the lumen of the elongate shaft 140. In some embodiments, the distal handle portion 114 may include a side port 118 in communication with the lumen of the elongate shaft 140. In some embodiments, the medical device 100 and/or the handle 110 may include the proximal port 116 and the side port 118. In some embodiments, the proximal port 116 and/or the side port 118 may include a Luer connector, a Y-connector, a one-way valve, or other suitable connection. In some embodiments, the elongate shaft 140 may include a plurality of lumens (e.g., a plurality of working channels) extending through the elongate shaft 140.

In some embodiments, the distal tip 142 of the elongate shaft 140 of the medical device 100 may include optics and illumination means disposed therein. The optics and illumination means may be configured to provide optical visualization of the area of the patient being treated and/or traversed by the distal tip 142. The handle 110 of the medical device 100 may include an electronics and/or optics connector 124 configured to connect the optics and illumination means of the medical device 100 to a controller, a monitor, a display, a computer, etc. Other configurations, including but not limited to wireless communications, are also contemplated.

The elongate shaft 140 may be configured as a ureteroscope shaft, a flexible ureteroscope shaft, a dual lumen flexible ureteroscope shaft, a cystoscope shaft, a duodenoscope shaft, colonoscope shaft, or other endoscopic shaft, for a desired use.

In some embodiments, the medical device 100 may include an actuatable medical instrument 190 configured to be slidably disposed within the lumen of the elongate shaft 140 and the proximal port 116. In some embodiments, the actuatable medical instrument 190 may be configured to be slidably disposed within the lumen of the elongate shaft 140 and the side port 118. In some embodiments, the actuatable medical instrument 190 may be configured to be slidably disposed in the lumen of the elongate shaft 140 and either one of the proximal port 116 or the side port 118. In some embodiments, the actuatable medical instrument 190 may be removed from the lumen of the elongate shaft 140 and the proximal port 116 and disposed in the lumen of the elongate shaft 140 and the side port 118 during a procedure. In some embodiments, the actuatable medical instrument 190 may be removed from the lumen of the elongate shaft 140 and the side port 118 and disposed in the lumen of the elongate shaft 140 and the proximal port 116 during a procedure. In some embodiments, a proximal end of the actuatable medical instrument 190 may be operably connected to a second actuation mechanism 170 secured to the proximal handle portion 112. In some embodiments, a distal end of the actuatable medical instrument 190 may be configured to be within the lumen of the elongate shaft 140 at, adjacent to, and/or within the distal tip 142 of the elongate shaft 140.

In some embodiments, the actuatable medical instrument 190 may include a laser fiber, a retrieval device such as a retrieval basket or net, a forceps, an immobilization device, a stone sweeping device, another end effector, etc. Other configurations and/or example actuatable medical instruments are also contemplated. In some embodiments, the actuatable medical instrument 190 may include an outer sheath 192 having a lumen extending therethrough. In some embodiments, the outer sheath 192 may have an annular strain relief 194 disposed about a proximal end of the outer sheath 192. In at least some embodiments, the actuatable medical instrument 190 may include an inner wire 196 (e.g., FIGS. 10-11) slidably disposed within the outer sheath 192. In some embodiments, the inner wire 196 may include an end effector 199 (e.g., FIG. 11) at and/or adjacent a distal end of the inner wire 196. In some embodiments, the end effector 199 may include and/or may be formed from a shape memory material. In some embodiments, the outer sheath 192 may be axially movable within and/or with respect to the annular strain relief 194. In some embodiments, the distal end of the actuatable medical instrument 190 and/or the inner wire 196 may be disposed within the lumen of the elongate shaft 140 at, adjacent to, and/or within the distal tip 142 of the elongate shaft 140 in a collapsed or closed configuration.

Figure 2:
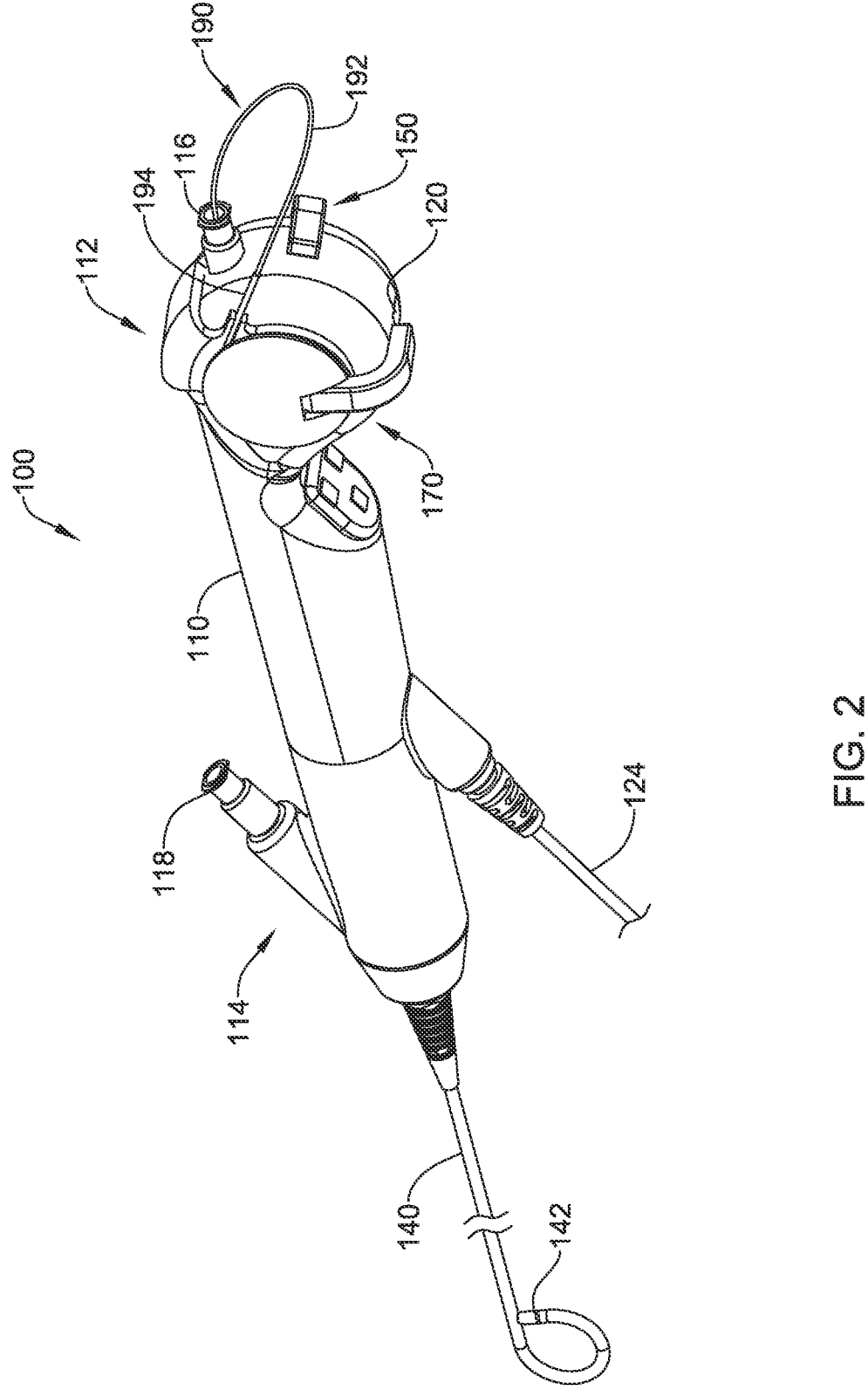

In some embodiments, the proximal handle portion 112 may include a deflection indicator 120 (see FIG. 2) disposed on an outside surface of the proximal handle portion 112. In some embodiments, the deflection indicator 120 may include a colored mark on the outside surface of the proximal handle portion 112. In some embodiments, the deflection indicator 120 may include a light and/or a light emitting diode (LED). The deflection indicator 120 may be adapted and configured to provide a visual warning to the user that the distal tip 142 is in the deflected configuration, as shown in FIG. 2. In some embodiments, when the distal tip 142 is disposed in a straightened configuration (e.g., not deflected), the deflection indicator 120 may be hidden (e.g., by a portion or component of the first actuation mechanism, etc.) and/or deactivated. In some embodiments, when the distal tip 142 is in the deflected configuration, (e.g., not straightened), the deflection indicator 120 may be visible and/or activated.

Figure 3:
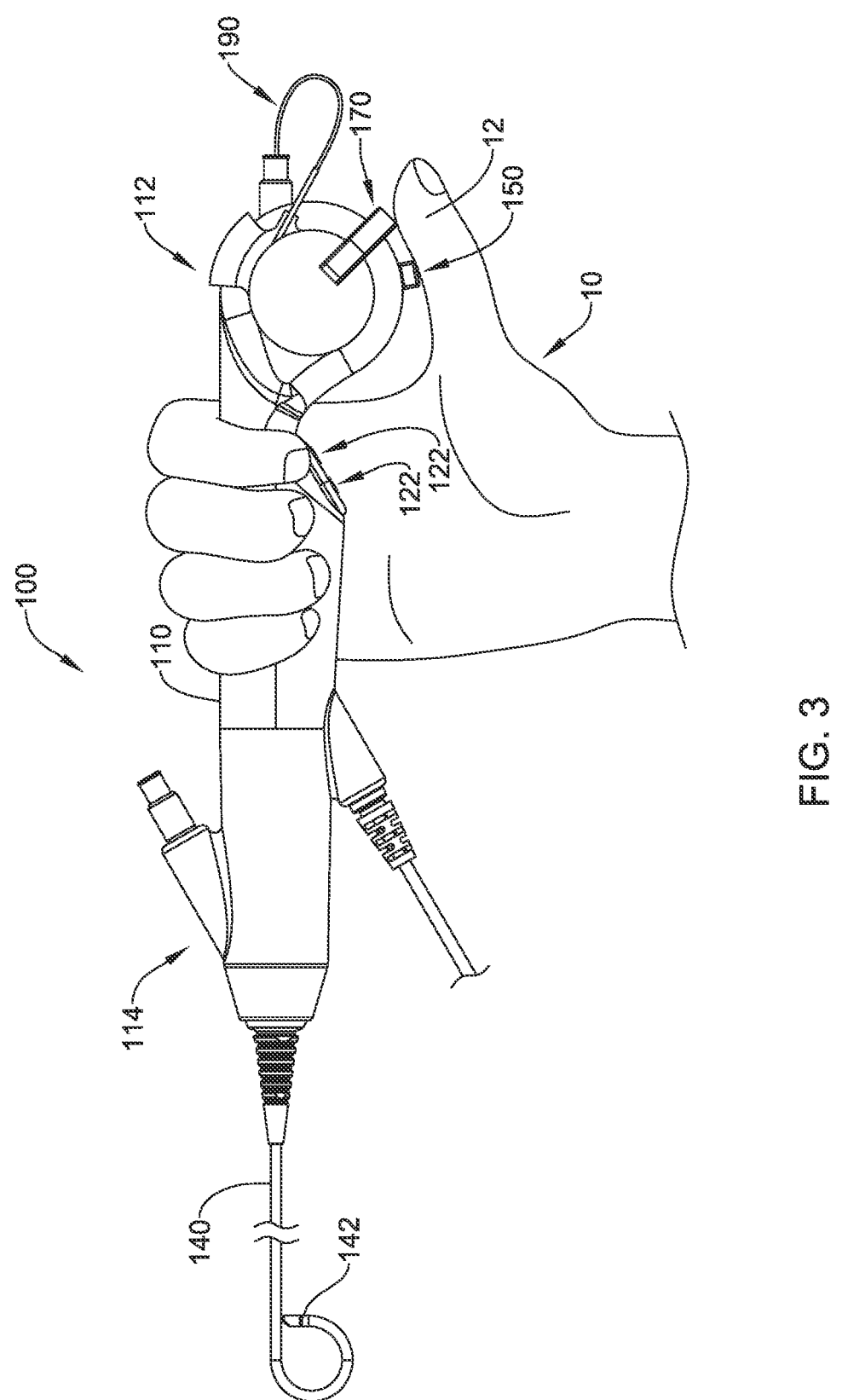
FIG. 3 illustrates the example medical device of FIGS. 1-2 being grasped by a user's hand.

The medical device 100 and/or the handle 110 may be adapted and configured to be grasped, held, and/or actuated using a first hand 10 of a user in a first position relative to the handle 110, as seen in FIG. 3. The first actuation mechanism 150 may be configured to be actuated by a thumb 12 of the first hand 10 in the first position relative to the handle 110, and the second actuation mechanism 170 may be configured to be actuated by the same thumb 12 of the first hand 10 in the first position relative to the handle 110. Accordingly, the medical device 100 may be configured to be actuated using a single hand (e.g., the first hand 10) in the first position relative to the handle 110. In some embodiments, a second hand (not shown) different from the first hand 10 may be used to advance and/or retract the actuatable medical instrument 190 and/or the outer sheath 192 relative to the elongate shaft 140 by grasping the outer sheath 192 proximal of the proximal port 116 (or the side port 118, where appropriate) with a thumb and forefinger of the second hand while the first hand 10 grasps and/or holds the handle 110.

In some embodiments, the handle 110 may include one or more buttons 122 configured to control and/or actuate various functions (e.g., irrigation, laser activation, suction, etc.) that may be associated with the medical device 100 and/or the procedure being performed. In some embodiments, the one or more buttons 122 may include and/or may be electronic controls. In some embodiments, the one or more buttons 122 may be positioned and/or configured to be actuated by the thumb 12 of the first hand 10 in the first position relative to the handle 110. In some embodiments, the one or more buttons 122 may be positioned and/or configured to be actuated by a finger of the first hand 10. In some alternative embodiments, the one or more buttons 122 may be positioned and/or configured to be actuated by a finger of a second hand (not shown).

In some embodiments, the medical device 100 and/or the handle 110 may include a second button pad including one or more buttons disposed generally opposite the one or more buttons 122 with respect to the longitudinal axis of the handle 110, which may be actuated using a forefinger of the first hand 10. In some embodiments, the one or more buttons of the second button pad may be configured to operate and/or actuate devices and/or features that may cause harm if activated inadvertently, such as a laser or a cautery device. In some embodiments, one of the one or more buttons 122 may need to be activated as a safety mechanism before the one or more buttons on the second button pad is or can be activated. Other configurations are also contemplated.

Figure 4:
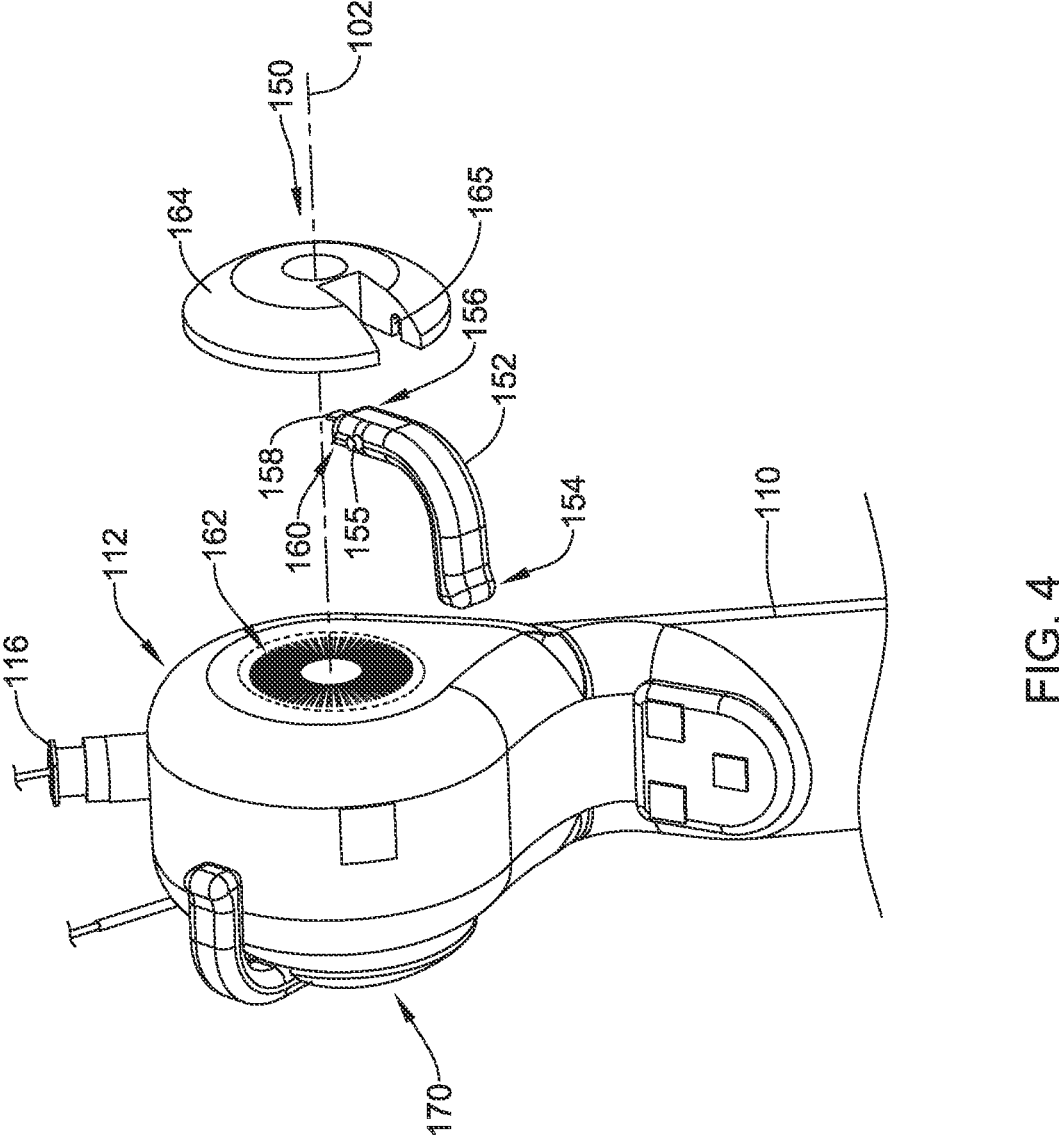
FIG. 4 is a partially exploded view of a first actuation mechanism associated with the example medical device.
Figure 5:
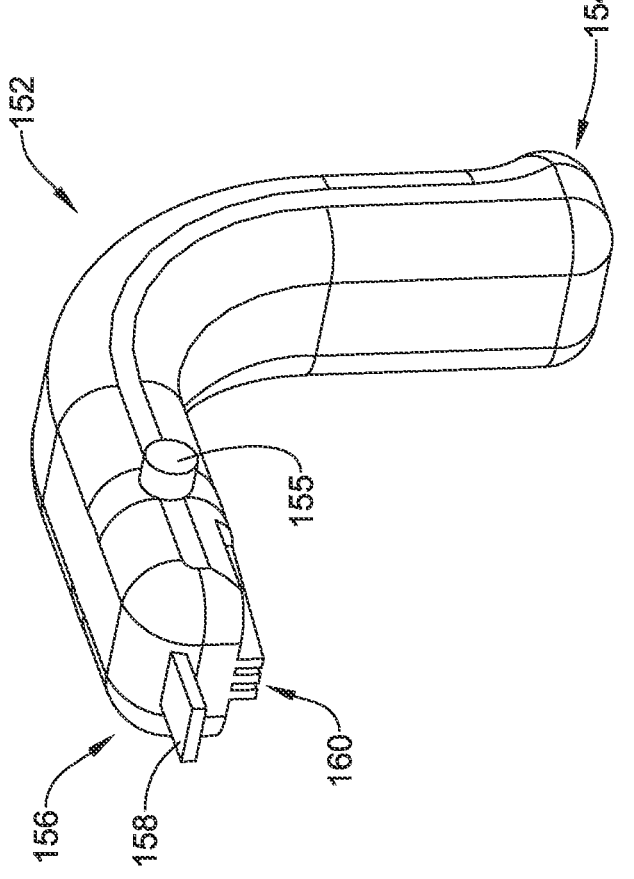
FIG. 5 illustrates aspects of a first hinged arm of the first actuation mechanism.

FIG. 4 is a partially exploded view illustrating selected aspects of the first actuation mechanism 150. In some embodiments, the first actuation mechanism 150 may include a first hinged arm 152 (shown in detail in FIG. 5) having a first free end 154 and a first hinged end 156 opposite the first free end 154, a first biasing element (e.g., spring) 158, and a first tooth 160 formed in the first hinged end 156 of the first hinged arm 152, the first tooth 160 being configured to releasably engage a first plurality of teeth 162 formed in the proximal handle portion 112. In some embodiments, the first tooth 160 may include and/or may be a plurality of teeth. In at least some embodiments, the first hinged arm 152 may be engaged with a cover 164. The cover 164 may be configured to be engaged with the proximal handle portion 112. The cover 164 and/or the first hinged arm 152 may be configured to rotate around a first axis of rotation 102 extending transversely through the proximal handle portion 112 substantially perpendicular to the longitudinal axis of the handle 110. In some embodiments, the cover 164 may be engaged with the proximal handle portion 112 via one or more protrusions, a snap fit, a friction fit, a mechanical engagement, or other suitable means.

In at least some embodiments, the first plurality of teeth 162 formed in the proximal handle portion 112 may be formed around the first axis of rotation 102. In some embodiments, the first plurality of teeth 162 formed in the proximal handle portion 112 may be formed around the first axis of rotation 102 in a continuous circular pattern or a semi-circular pattern, for example. In some embodiments, the first plurality of teeth 162 formed in the proximal handle portion 112 may be formed around the first axis of rotation 102 in a discontinuous circular pattern. Other configurations are also contemplated.

Figure 6:
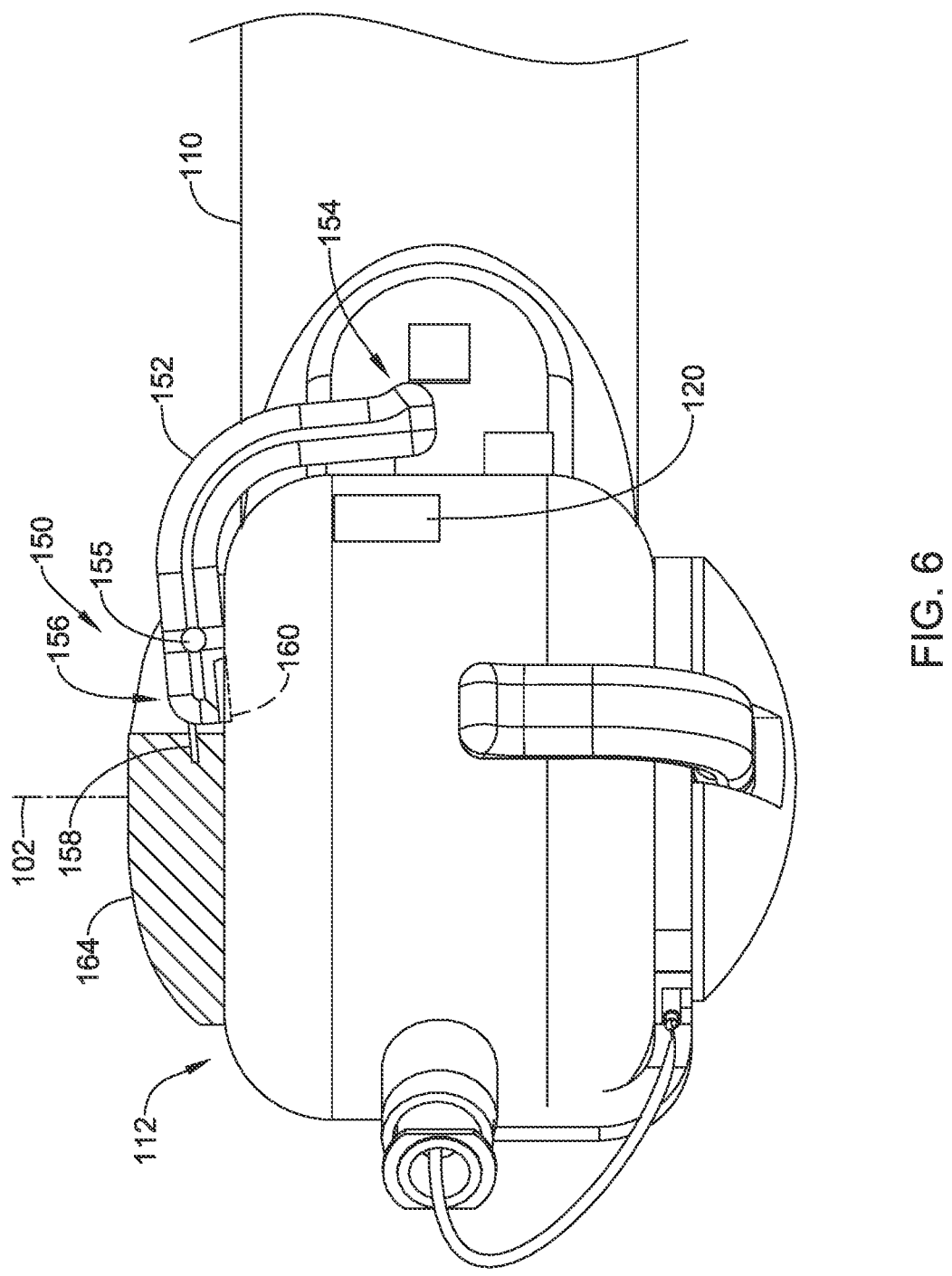
FIGS. 6-7 illustrate aspects of actuating the first actuation mechanism.

The first hinged arm 152 may include one or more projections 155 extending outward from the first hinged arm 152. The one or more projections 155 may form and/or define a first pivot axis of the first hinged arm 152 relative to the cover 164 and/or the handle 110. In at least some embodiments, the one or more projections 155 may be configured to be received by and/or to engage one or more recesses 165 formed in the cover 164. The first biasing element 158 may be configured to bias the first hinged arm 152 about the first pivot axis of the first hinged arm 152. The first biasing element 158 may be configured to bias the first hinged arm 152 toward a first locked position, wherein the first free end 154 of the first hinged arm 152 is biased away from the handle 110, as shown in FIG. 6. In the first locked position, the first tooth 160 and/or the first hinged end 156 of the first hinged arm 152 may be biased toward the handle 110 and/or engaged with the first plurality of teeth 162 (not shown). Accordingly, in at least some embodiments, the first actuation mechanism 150 may be self-locking. In the first locked position, the first actuation mechanism 150 and/or the first hinged arm 152 is prevented from rotating relative to the proximal handle portion 112 with the first tooth 160 engaged with the first plurality of teeth 162.

In some embodiments, a first end of the first biasing element 158 may be fixedly attached to, disposed within, and/or embedded within the first hinged end 156 of the first hinged arm 152. A second end of the first biasing element 158 opposite the first end of the first biasing element 158 may be configured to engage the cover 164 (shown in partial section). In at least some embodiments, the cover 164 may include a slot sized and configured to slidably receive the second end of the first biasing element 158.

In an alternative configuration, a first end of the first biasing element 158 may be fixedly attached to, disposed within, and/or embedded within the cover 164. A second end of the first biasing element 158 opposite the first end of the first biasing element 158 may be configured to engage the first hinged end 156 of the first hinged arm 152. In at least some embodiments, the first hinged end 156 of the first hinged arm 152 may include a slot sized and configured to slidably receive the second end of the first biasing element 158.

In some embodiments, the first biasing element 158 may include a flat spring and/or a strip of resilient material. In some embodiments, the first biasing element 158 may be formed from polymeric, metallic, and/or composite materials including but not limited to stainless steel, nickel-titanium alloy, etc. Some examples of suitable but non-limiting materials are discussed below.

Figure 7:
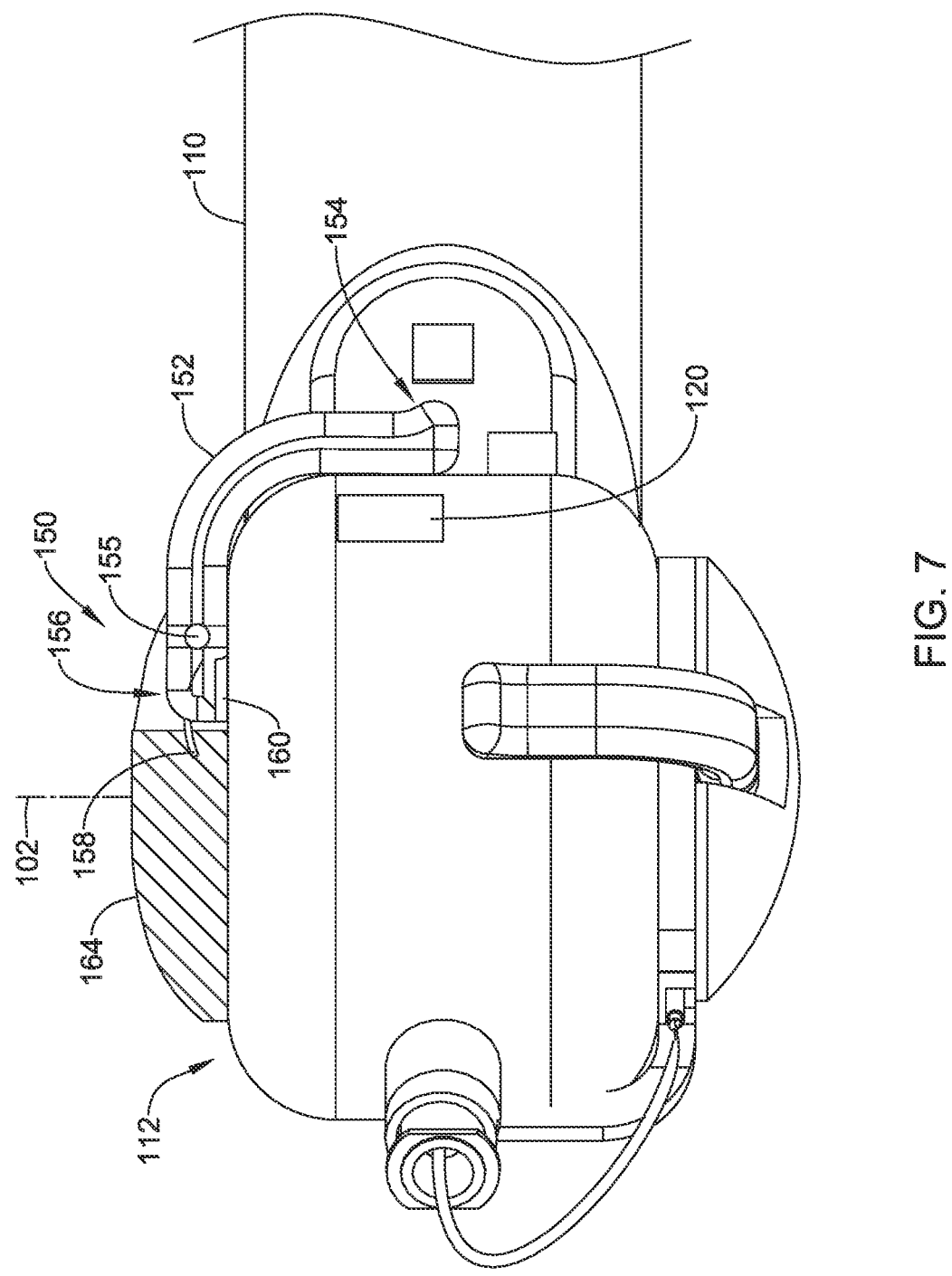

When the first free end 154 of the first hinged arm 152 of the first actuation mechanism 150 is pressed toward the handle 110, by the thumb 12 of the first hand 10 for example, the first hinged arm 152 may be moved out of the first locked position and toward a first, unlocked actuation position. When the first free end 154 of the first hinged arm 152 of the first actuation mechanism 150 is pressed toward the handle 110, the first biasing element 158 may bend and/or deflect as the first hinged arm 152 pivots about the first pivot axis and/or the one or more projections 155, thereby moving the first tooth 160 away from the handle 110, as shown in FIG. 7, and/or disengaging the first tooth 160 from the first plurality of teeth 162 (not shown). As such, in the first actuation position, the first tooth 160 may be translated outward away from the handle 110 and/or the first tooth 160 may be disengaged from the first plurality of teeth 162 (not shown), and permitting the first hinged arm 152 to be rotatable about the first axis of rotation 102 along with the cover 164.

When the first hinged arm 152 of the first actuation mechanism 150 is disposed in a home position relative to the proximal handle portion 112, the first hinged arm 152 may be disposed over and/or may cover the deflection indicator 120 so that the deflection indicator 120 is hidden from view (e.g., FIG. 1). When the first hinged arm 152 of the first actuation mechanism 150 is disposed in the home position, the distal tip 142 may be in the straightened configuration. When the first hinged arm 152 of the first actuation mechanism 150 is rotated about the first axis of rotation 102 and moved away from the home position relative to the proximal handle portion 112, the deflection indicator 120 may be visible to the user and/or the distal tip 142 may be in the deflected configuration (e.g., FIG. 2).

Figure 8:
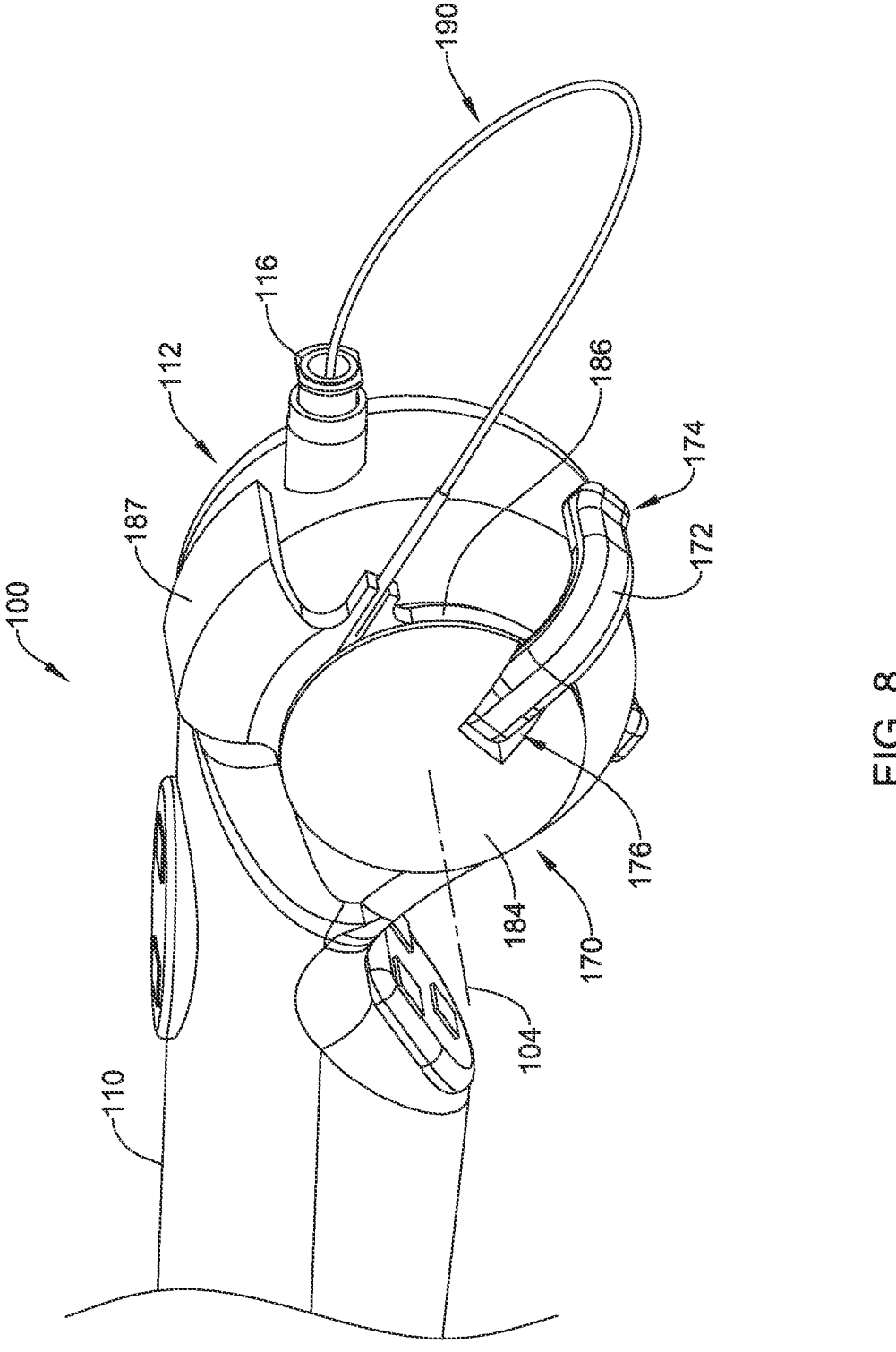
FIG. 8 illustrates aspects of a second actuation mechanism associated with the example medical device.
Figure 9:
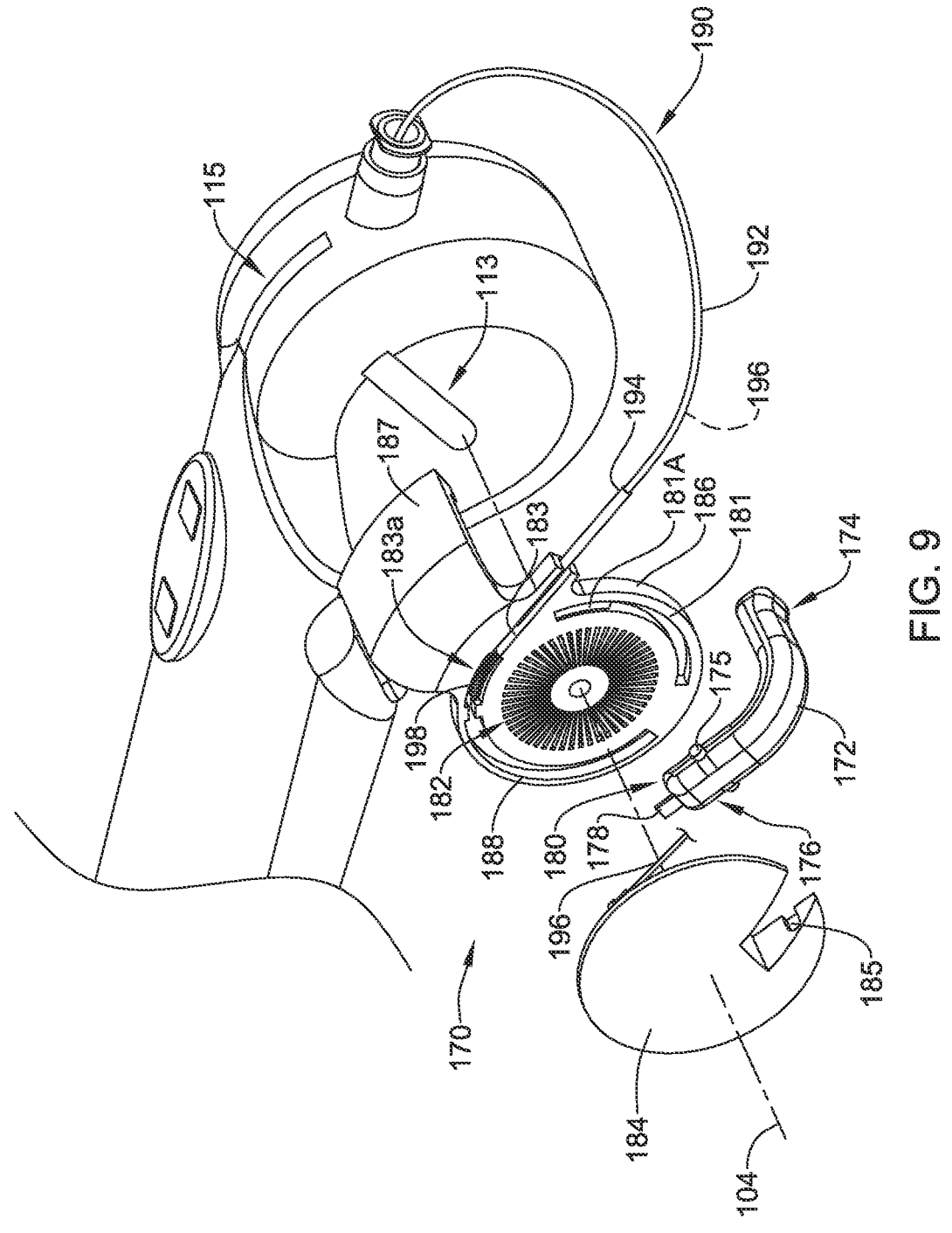
FIG. 9 is a partially exploded view of the second actuation mechanism.

FIG. 8 illustrates selected aspects of the second actuation mechanism 170 secured to the proximal handle portion 112 of the handle 110, and FIG. 9 is a partially exploded view of selected aspects of the second actuation mechanism 170. The medical device 100 may include the actuatable medical instrument 190 configured to be slidably disposed within the elongate shaft 140 (not shown) and the proximal port 116. The actuatable medical instrument 190 may be operably connected to the second actuation mechanism 170. The second actuation mechanism 170 may include an actuation housing comprising a base portion 186 and a cover portion 184 configured to rotate relative to the base portion 186. The base portion 186 may include an extension 187 configured to extend around at least a portion of the proximal handle portion 112. In at least some embodiments, the extension 187 may include a flange extending transversely therefrom configured to engage a slot 115 formed in an outer surface of the proximal handle portion 112. In some embodiments, the slot 115 may extend longitudinally and/or generally parallel to the longitudinal axis of the handle 110. In some embodiments, engagement of the flange of the extension 187 with the slot 115 may rotatably secure the base portion 186 relative to the proximal handle portion 112 of the handle 110. As such, the base portion 186 may be prevented from rotating relative to the proximal handle portion 112. In some embodiments, the actuation housing and/or the base portion 186 may be removably secured to the proximal handle portion 112. In some embodiments, the base portion 186 may include a securing element (not shown) extending from a back side of the base portion 186, wherein the securing element is configured to slidably engage a mounting slot 113 formed in the proximal handle portion 112. Other engagement means such as snap fit, friction fit, twist lock, etc. are also contemplated.

In some embodiments, the second actuation mechanism 170 may include a second hinged arm 172 (similar to the first hinged arm 152 shown in FIG. 5) having a second free end 174 and a second hinged end 176 opposite the second free end 174, a second biasing element (e.g., spring) 178, and a second tooth 180 formed in the second hinged end 176 of the second hinged arm 172, the second tooth 180 being configured to releasably engage a second plurality of teeth 182 formed in the base portion 186. In some embodiments, the second tooth 180 may include and/or may be a plurality of teeth. In at least some embodiments, the second hinged arm 172 may be engaged with the cover portion 184. The cover portion 184 may be configured to be rotatably engaged with the base portion 186 and/or the proximal handle portion 112 of the handle 110. The cover portion 184 and/or the second hinged arm 172 may be configured to rotate around a second axis of rotation 104 extending transversely through the proximal handle portion 112 substantially perpendicular to the longitudinal axis of the handle 110. In some embodiments, the second axis of rotation 104 may be parallel to and/or coaxial with the first axis of rotation 102 (e.g., FIG. 4). In some embodiments, the cover portion 184 may be engaged with the base portion 186 via one or more protrusions, a snap fit, a friction fit, a mechanical engagement, or other suitable means. In some embodiments, the cover portion 184 may be removably secured, connected, and/or attached to the proximal handle portion 112 via the mounting slot 113, and the cover portion 184 may removably secure the base portion 186 and/or the actuation housing to the proximal handle portion 112 via the mounting slot 113. For example, a securement element of the cover portion 184 configured to removably secure the cover portion 184 to the proximal handle portion 112 may extend through an aperture formed in the base portion 186. Other configurations are also contemplated.

In at least some embodiments, the second plurality of teeth 182 formed in the base portion 186 may be formed around the second axis of rotation 104. In some embodiments, the second plurality of teeth 182 formed in the base portion 186 may be formed around the second axis of rotation 104 in a continuous circular pattern or a semi-circular pattern, for example. In some embodiments, the second plurality of teeth 182 formed in the base portion 186 may be formed around the second axis of rotation 104 in a discontinuous circular pattern. Other configurations are also contemplated.

The second hinged arm 172 may include one or more projections 175 extending outward from the second hinged arm 172. The one or more projections 175 may form and/or define a second pivot axis of the second hinged arm 172 relative to the cover portion 184 and/or the handle 110. In at least some embodiments, the one or more projections 175 may be configured to be received by and/or to engage one or more recesses 185 formed in the cover portion 184. The second biasing element 178 may be configured to bias the second hinged arm 172 about the second pivot axis of the second hinged arm 172. The second biasing element 178 may be configured to bias the second hinged arm 172 toward a second locked position, wherein the second free end 174 of the second hinged arm 172 is biased away from the handle 110, as shown with respect to the first hinged arm 152 in FIG. 6. In the second locked position, the second tooth 180 and/or the second hinged end 176 of the second hinged arm 172 may be biased toward the handle 110 and/or engaged with the second plurality of teeth 182. Accordingly, in at least some embodiments, the second actuation mechanism 170 may be self-locking. In the second locked position, the second actuation mechanism 170 and/or the second hinged arm 172 is prevented from rotating relative to the base portion 186 and/or the proximal handle portion 112 with the second tooth 180 engaged with the second plurality of teeth 182.

In some embodiments, a first end of the second biasing element 178 may be fixedly attached to, disposed within, and/or embedded within the second hinged end 176 of the second hinged arm 172. A second end of the second biasing element 178 opposite the first end of the second biasing element 178 may be configured to engage the cover portion 184 as shown with respect to the first biasing element 158 in FIGS. 6-7. In at least some embodiments, the cover portion 184 may include a slot sized and configured to slidably receive the second end of the second biasing element 178.

In an alternative configuration, a first end of the second biasing element 178 may be fixedly attached to, disposed within, and/or embedded within the cover portion 184. A second end of the second biasing element 178 opposite the first end of the second biasing element 178 may be configured to engage the second hinged end 176 of the second hinged arm 172. In at least some embodiments, the second hinged end 176 of the second hinged arm 172 may include a slot sized and configured to slidably receive the second end of the second biasing element 178.

In some embodiments, the second biasing element 178 may include a flat spring and/or a strip of resilient material. In some embodiments, the second biasing element 178 may be formed from polymeric, metallic, and/or composite materials including but not limited to stainless steel, nickel-titanium alloy, etc. Some examples of suitable but non-limiting materials are discussed below.

When the second free end 174 of the second hinged arm 172 of the second actuation mechanism 170 is pressed toward the handle 110, by the thumb 12 of the first hand 10 for example, the second hinged arm 172 may be moved out of the second locked position and toward a second, unlocked actuation position. When the second free end 174 of the second hinged arm 172 of the second actuation mechanism 170 is pressed toward the handle 110, the second biasing element 178 may bend and/or deflect as the second hinged arm 172 pivots about the second pivot axis and/or the one or more projections 175, thereby moving the second tooth 180 away from the base portion 186 and/or the handle 110, as shown with respect to the first actuation mechanism in FIG. 7, and/or disengaging the second tooth 180 from the second plurality of teeth 182. As such, in the second actuation position, the second tooth 180 may be translated outward away from the handle 110 and/or the second tooth 180 may be disengaged from the second plurality of teeth 182, and permitting the second hinged arm 172 to be rotatable about the second axis of rotation 104 along with the cover portion 184.

As discussed herein, the actuatable medical instrument 190 may include the inner wire 196. In FIG. 9, a proximal end of the inner wire 196 is shown engaged with and/or attached to the cover portion 184 of the actuation housing of the second actuation mechanism 170. The inner wire 196 may be longitudinally slidable within the outer sheath 192 of the actuatable medical instrument 190. As the second hinged arm 172 and the cover portion 184 rotate together about the second axis of rotation 104, the inner wire 196 may be translated longitudinally and/or axially relative to the outer sheath 192. As such, the second actuation mechanism 170 may be configured to actuate and/or translate the end effector 199 (e.g., FIG. 11) at the distal end of the inner wire 196 through longitudinal movement of the inner wire 196 relative to the outer sheath 192. The base portion 186 of the actuation housing includes an actuation slot 188 formed therein. A proximal portion of the inner wire 196 may extend within the actuation slot 188 between the outer sheath 192 and the proximal end of the inner wire 196 engaged and/or connected to the cover portion 184.

As may also be seen in FIG. 9, the base portion 186 may include a stroke limiter slot 181 formed therein. The stroke limiter slot 181 may be configured to receive and/or engage a stroke length projection 181B (e.g., FIG. 10) extending from a bottom of the cover portion 184. The stroke limiter slot 181 may be configured to limit translation (e.g., rotational translation, etc.) and/or stroke length of the second hinged arm 172 and the cover portion 184 relative to the base portion 186 and/or the proximal handle portion 112. In some embodiments, a stroke limiter element 181A may be disposed within the stroke limiter slot 181. The stroke limiter element 181A may be exchangeable and/or replaceable to accommodate different sizes of the end effector 199 (e.g., FIG. 11) at the distal end of the inner wire 196 and/or the actuatable medical instrument 190. The end limits of the stroke limiter slot 181 (with or without the stroke limiter element 181A, depending upon the end effector 199) may permit a fully opened and a fully closed end effector 199. In other embodiments, the second actuation mechanism may include a different stroke limiting mechanism, such as a projection moving between end stops, etc.

In some embodiments, the base portion 186 of the actuation housing of the second actuation mechanism 170 may include a mounting slot 183 configured to receive the proximal end of the outer sheath 192 and/or a proximal end of the annular strain relief 194 therein. In some embodiments, the proximal end of the annular strain relief 194 of the actuatable medical instrument 190 may be fixedly attached to the base portion 186 of the actuation housing of the second actuation mechanism 170 and the inner wire 196 may be engaged with, connected to, and/or attached to the cover portion 184 of the actuation housing of the second actuation mechanism 170. For example, the cover portion 184 of the actuation housing may include an actuation projection 189 (e.g., FIG. 10) extending from the bottom of the cover portion 184 and configured to be received in the actuation slot 188. The proximal end of the inner wire 196 may be engaged with, connected to, and/or attached to the actuation projection 189 such that rotation of the second hinged arm 172 and the cover portion 184 causes axially translation of the inner wire 196 relative to the outer sheath 192 of the actuable medical instrument 190. In some embodiments, the proximal end of the outer sheath 192 may be fixedly attached to the base portion 186 of the actuation housing.

In some embodiments, the outer sheath 192 may be axially movable within the annular strain relief 194. In some embodiments, the outer sheath 192 may include a stop 193 (e.g., FIG. 10) fixed at the proximal end of the outer sheath 192. In some embodiments, the second actuation mechanism 170 may optionally include a compression spring 198 associated with the proximal end of the actuable medical instrument 190 and/or the proximal end of the outer sheath 192. The compression spring 198 may be disposed within an enlarged portion of the mounting slot 183 (e.g., secondary slot 183A) in communication with the mounting slot 183 and/or the actuation slot 188. In at least some embodiments, the proximal portion of the inner wire 196 may extend from the proximal end of the outer sheath 192 through the compression spring 198 within the secondary slot 183A and into the actuation slot 188. In some embodiments, the stop 193 may be disposed within the enlarged portion of the mounting slot 183 (e.g., secondary slot 183A). The compression spring 198 may be configured to bias the stop 193 and/or the outer sheath 192 toward a distal end of the mounting slot 183 and/or the secondary slot 183A.

Figure 10:
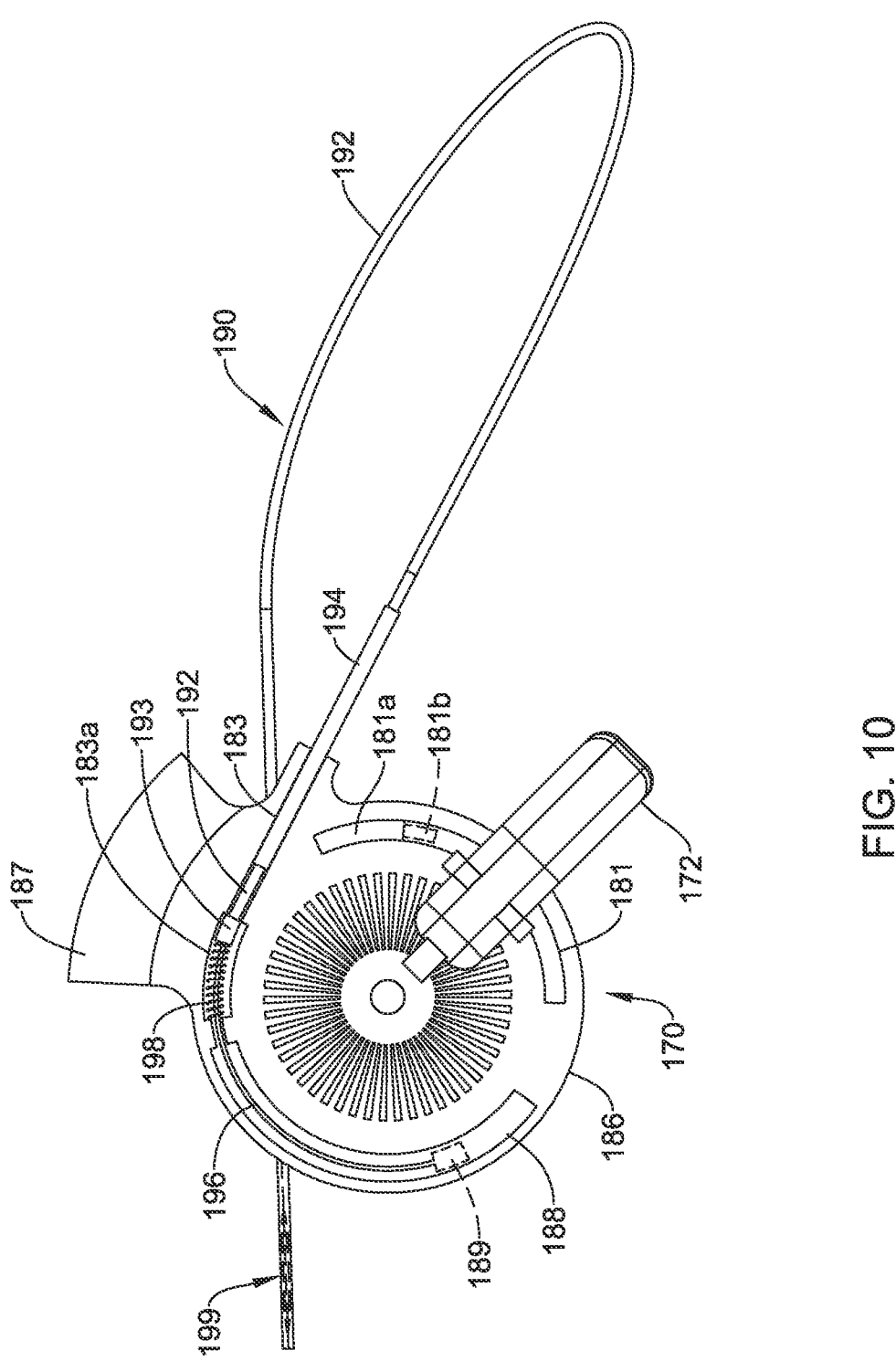
FIG. 10 illustrates aspects of an actuatable medical instrument associated with the second actuation mechanism in a collapsed configuration.
Figure 11:
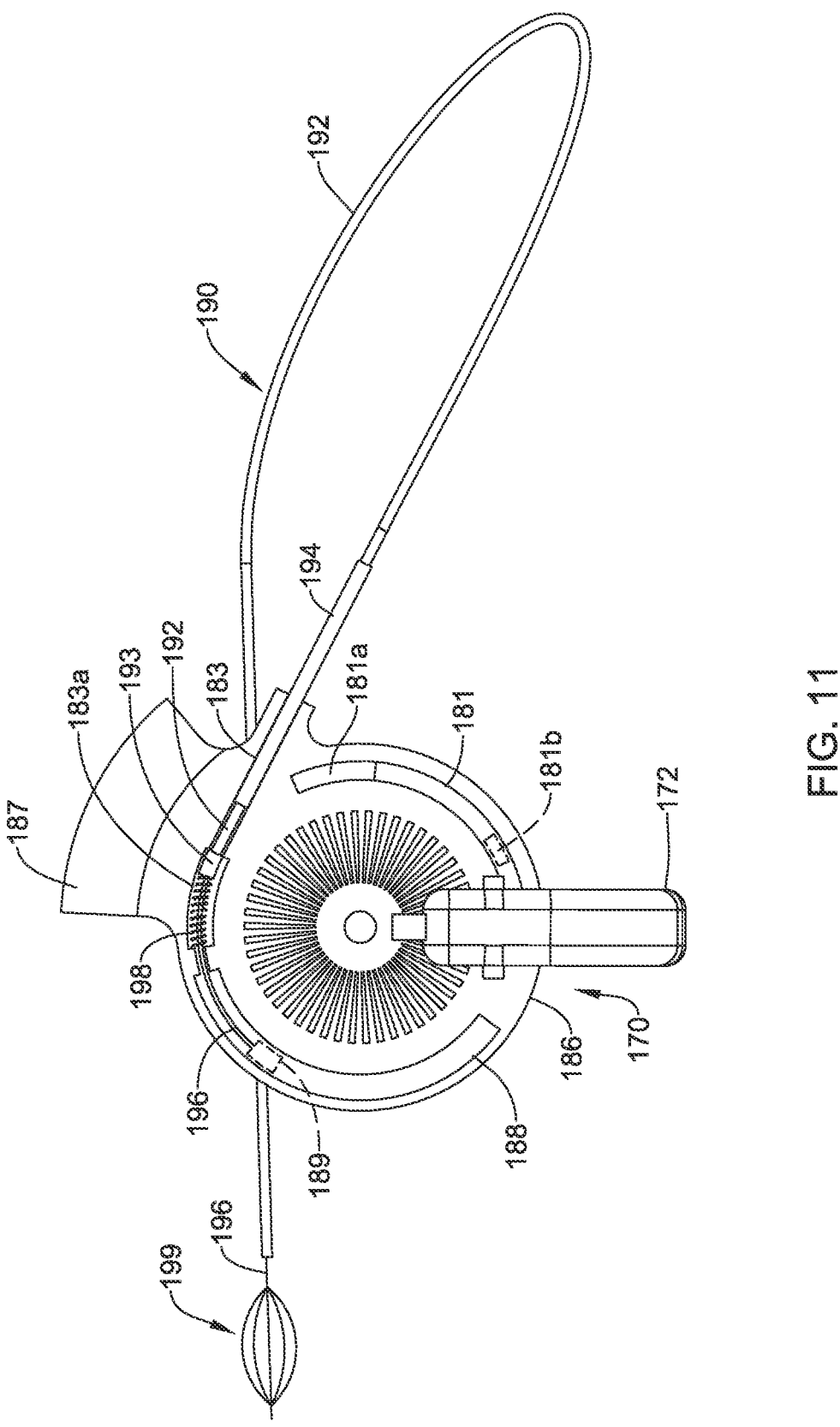
FIG. 11 illustrates aspects of the actuatable medical instrument associated with the second actuation mechanism in an expanded configuration.
Figure 12:
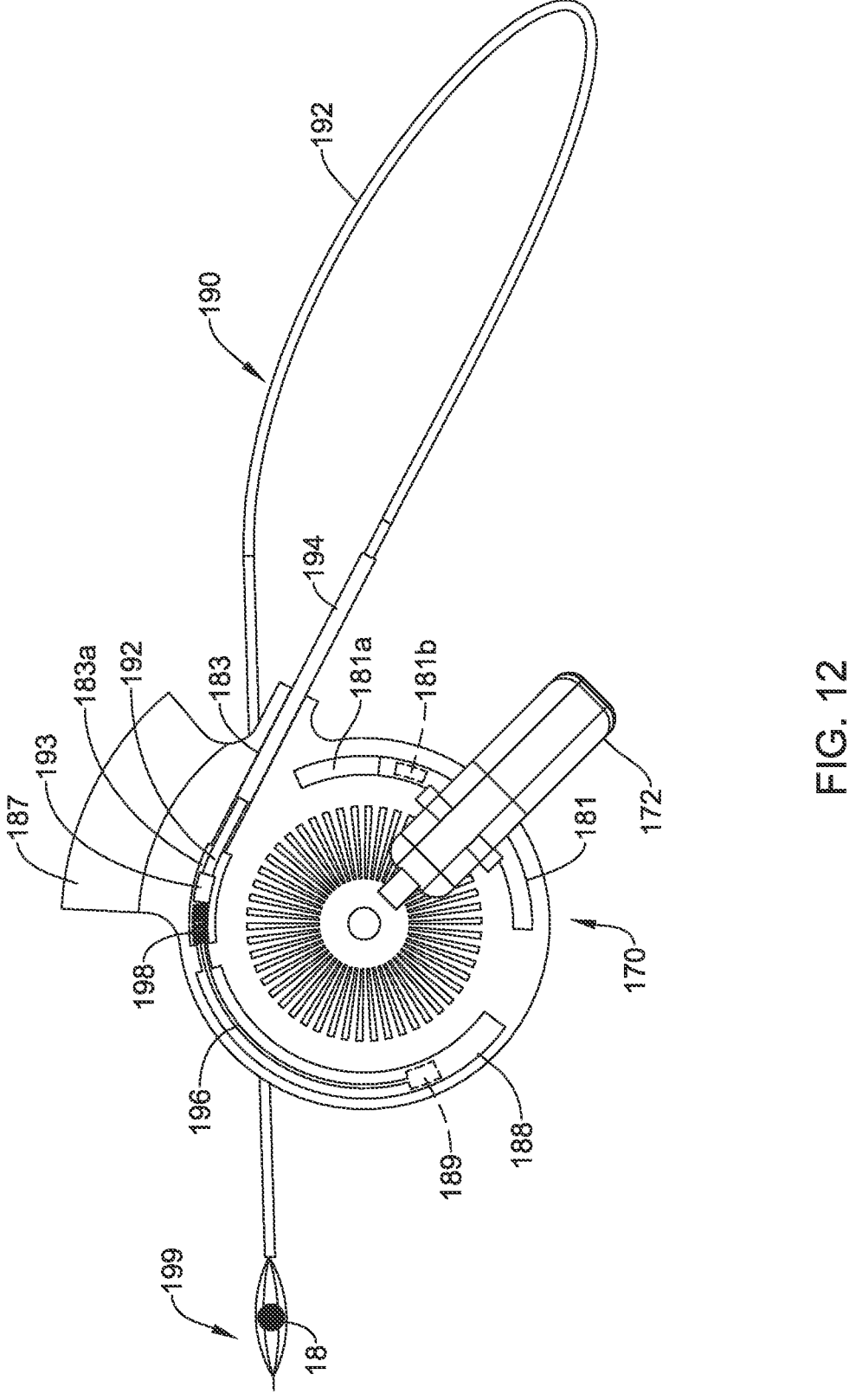
FIG. 12 illustrates aspects of the actuatable medical instrument associated with the second actuation mechanism in a partially collapsed configuration.

FIGS. 10-12 illustrate aspects of the operation of the second actuation mechanism 170 and the actuable medical instrument 190. For clarity, some elements of the second actuation mechanism 170 are not shown. In at least some embodiments, the second actuation mechanism 170 and the actuable medical instrument 190 may be formed as a sub-assembly that may be interchanged and/or replaced on the medical device 100 as needed. As discussed herein, the actuable medical instrument 190 may include an end effector 199 (e.g., FIG. 11) disposed at the distal end of the inner wire 196. In FIG. 10, the end effector 199 is disposed in a collapsed configuration. When the distal tip 142 of the elongate shaft 140 is positioned at an area of interest for treatment, the second actuation mechanism 170 may be used to expand, or otherwise deploy the end effector 199.

The following description is made with the second actuation mechanism 170 oriented such that the cover portion 184 (not shown) faces toward the user. The skilled artisan will recognize that the medical device 100 and/or the second actuation mechanism 170 does not need to be so oriented and/or positioned during use. Instead, the above reference to orientation of the second actuation mechanism 170 is provided merely for context and is not intended to be limiting. The thumb 12 of the first hand 10 (e.g., FIG. 3) may be used to translate, move, and/or actuate the second hinged arm 172 of the second actuation mechanism 170. The thumb 12 may press and hold the second hinged arm 172 of the second actuation mechanism 170 inward toward the handle 110 (not shown) to unlock the second actuation mechanism 170 by disengaging the second tooth 180 (not shown) from the second plurality of teeth 182. The thumb 12 may then translate and/or rotate the second hinged arm 172 of the second actuation mechanism 170 relative to the base portion 186 and/or the proximal handle portion 112, while the second actuation mechanism 170 is unlocked, to actuate and/or longitudinally translate the inner wire 196 of the actuable medical instrument 190 relative to the outer sheath 192 of the actuable medical instrument 190. FIG. 10 illustrates the end effector 199 disposed within the distal end of the outer sheath 192 in a collapsed configuration and thus may be considered to define a home position of the second hinged arm 172 of the second actuation mechanism 170.

As shown in FIG. 10, the proximal portion of the inner wire 196 extends within the secondary slot 183A and the actuation slot 188 from the proximal end of the outer sheath 192 and/or the stop 193 to the actuation projection 189. The proximal end of the inner wire 196 may be engaged with, connected to, and/or attached to the actuation projection 189, which extends from the cover portion 184 distally (as viewed) and/or in a direction away from the user into the actuation slot 188. As such, when the second hinged arm 172 of the second actuation mechanism 170 and the cover portion 184 is rotated relative to the base portion 186, the actuation projection 189 is translated within the actuation slot 188 along an arcuate path in the same direction that the second hinged arm 172 of the second actuation mechanism 170 and/or the cover portion 184 is rotated. For example, FIG. 11 illustrates the second actuation mechanism 170 after the second hinged arm 172 of the second actuation mechanism 170 and the cover portion 184 (not shown) have been rotated in a clockwise direction relative to the base portion 186. Accordingly, the actuation projection 189 extending from the cover portion 184 has been rotated in a clockwise direction within the actuation slot 188. Since the proximal end of the inner wire 196 is engaged with, connected to, and/or attached to the actuation projection 189, the inner wire 196 is also translated in the same clockwise direction, which therefore translates the inner wire 196 distally within the outer sheath 192 to deploy the end effector 199 out the distal end of the outer sheath 192. Releasing the second hinged arm 172 of the second actuation mechanism 170 causes the second biasing element 178 to urge the second hinged arm 172 of the second actuation mechanism 170 back to the second locked position wherein the second tooth 180 is engaged with the second plurality of teeth 182.

In some embodiments, the end effector 199 may be configured to expand to an expanded configuration when deployed and/or unconstrained. In some embodiments, the end effector 199 may be biased toward the expanded configuration. In some embodiments, the end effector 199 may be self-biased toward the expanded configuration. As such, in at least some embodiments, the end effector 199 may be self-expanding. In the illustrated example, the end effector 199 is shown as a retrieval basket or cage configured to capture a kidney stone or other debris. However, other end effector configurations are also contemplated.

Similar to the movement of the actuation projection 189 within the actuation slot 188, the operation and movement of the stroke limiting feature of the second actuation mechanism 170 may also be seen in FIGS. 10-12. As discussed herein, the base portion 186 of the second actuation mechanism 170 may include the stroke limiter slot 181 formed therein. The stroke limiter slot 181 may be configured to receive and/or engage the stroke length projection 181B extending from the cover portion 184 distally (as viewed) and/or in the direction away from the user into the stroke limiter slot 181. The stroke limiter slot 181 may be configured to limit translation (e.g., rotational translation, etc.) and/or stroke length of the second hinged arm 172 and the cover portion 184 (not shown) relative to the base portion 186 and/or the proximal handle portion 112. In some embodiments, the stroke limiter element 181A may be disposable within the stroke limiter slot 181 and may be exchangeable and/or replaceable to accommodate different sizes of the end effector 199 at the distal end of the inner wire 196 and/or the actuatable medical instrument 190. The end limits of the stroke limiter slot 181 (with or without the stroke limiter element 181A, depending upon the end effector 199) may permit the end effector 199 to fully expand and to fully retract. In some embodiments, it may be beneficial to limit retraction of the end effector 199 and/or the inner wire 196. As such, the stroke limiter element 181A may have a longer length, thereby reducing how far the inner wire 196 and/or the end effector 199 may be retracted by engaging the stroke length projection 181B and preventing the second hinged arm 172 and the cover portion 184 from rotating counterclockwise relative to the base portion 186 past a desired position.

In some embodiments, the second actuation mechanism 170 may include the compression spring 198 disposed within the mounting slot 183 and/or the enlarged portion of the mounting slot 183 (e.g., secondary slot 183A). The compression spring 198 may be disposed along, over, on, and/or around the proximal portion of the inner wire 196. The compression spring 198 may be configured to engage a proximal end of the mounting slot 183 and/or the enlarged portion of the mounting slot 183 (e.g., secondary slot 183A), and the compression spring 198 may be configured to engage the stop 193 fixed at the proximal end of the outer sheath 192. As discussed herein, the compression spring 198 may be configured to bias the outer sheath 192 and/or the stop 193 toward the distal end of the mounting slot 183 and/or the enlarged portion of the mounting slot 183 (e.g., secondary slot 183A). Similarly, the compression spring 198 may be configured to permit and/or resist axial translation of the stop 193 and/or the outer sheath 192 proximally within the mounting slot 183 and/or the enlarged portion of the mounting slot 183 (e.g., secondary slot 183A). In some embodiments, the outer sheath 192 may be axially movable and/or translatable within the annular strain relief 194. In some embodiments, this may be useful when capturing debris 18 (e.g., FIG. 12), such as a kidney stone, etc., having an outer diameter greater than an inner diameter of the outer sheath 192. Attempting to forcibly retract the inner wire 196 and/or the end effector 199 while holding the debris 18 may cause undesirable compressive force to develop within the outer sheath 192, may cause damage to the distal end of the outer sheath 192 and/or the end effector 199, and/or may cause injury to the patient.

Accordingly, in some embodiments, when the end effector 199 has been used to capture debris 18 and/or when the end effector 199 encounters resistance to retraction at the distal end of the outer sheath 192, the second actuation mechanism 170 may be configured to permit the outer sheath 192 to translate proximally within the mounting slot 183 and/or the enlarged portion of the mounting slot 183 (e.g., secondary slot 183A), as seen in FIG. 12. The compression spring 198 may be configured to provide resistance to proximal translation of the outer sheath 192, thereby acting as a "shock absorber". When the end effector 199 is retracted, a proximally directed force may be exerted against the compression spring 198 by the outer sheath 192 and/or the stop 193 fixed at the proximal end of the outer sheath 192. The compression spring 198 may be configured to exert a restorative force against the outer sheath 192 and/or the stop 193 fixed at the proximal end of the outer sheath 192. When the proximally directed force exceeds and/or is greater than the restorative force of the compression spring 198, the compression spring 198 may be compressed and/or displaced proximally by the outer sheath 192 and/or the stop 193 fixed at the proximal end of the outer sheath 192. As such, the outer sheath 192 may axially move and/or translate proximally within the annular strain relief 194. The compression spring 198 may be configured to compress at a known rate which may be used to limit the maximum allowable load between the outer sheath 192 and the end effector 199. In at least some embodiments, the maximum allowable load is preferred to be less than a break strength of the outer sheath 192 and/or less than a break strength of the end effector 199, whichever may be less. The compression spring 198 and associated movements within the second actuation mechanism 170 may permit the end effector 199 to be partially collapsed against the distal end of the outer sheath 192 and/or the distal tip 142 of the elongate shaft 140 to capture and hold the debris 18 distal of the distal end of the outer sheath 192 and/or the distal tip 142 of the elongate shaft 140 as the medical device 100 is withdrawn from the patient.

In an alternative configuration, the second actuation mechanism 170 may be configured to be non-self-locking. As such, the second actuation mechanism 170 may lack and/or be devoid of the second biasing element 178. Additionally, the end effector 199 may be configured to be self-closing and/or may be biased toward the collapsed configuration. In one example, a second compression spring (not shown) may be disposed along, over, on, and/or around the inner wire 196 within the actuation slot 188. The second compression spring may be disposed between a distal end of the actuation slot 188 of the base portion 186 and the actuation projection 189 of the cover portion 184. The second compression spring may be configured to bias the actuation projection 189 away from the distal end of the actuation slot 188 when the second actuation mechanism 170 and/or the second hinged arm 172 is released by the first hand 10. The second compression spring may be configured to return the second hinged arm 172 and/or the cover portion 184 to a home position. In doing so, the inner wire 196 will be retracted relative to the outer sheath 192 and/or the end effector 199 may be moved toward and/or to the collapsed configuration. If desired, the second hinged arm 172 may be provided with a manual locking mechanism to permit the second hinged arm 172 to maintain a displaced position away from the home position when the manual locking mechanism is engaged.

FIGS. 13-26 illustrate selected aspects of the medical device 100 and/or the first actuation mechanism 150. For clarity, some elements of the medical device 100 and/or the first actuation mechanism 150 are not shown or are not shown in their entirety. Additionally, some features such as but not limited to the handle 110 may vary in shape and/or configuration. In some embodiments, the medical device 100 may include a proximal portion 144 of the elongate shaft 140 disposed and/or extending longitudinally within the handle 110. The proximal portion 144 of the elongate shaft 140 may be in fluid communication with the proximal port 116 and/or the side port 118.

Figures 13, 14, 15, 16:
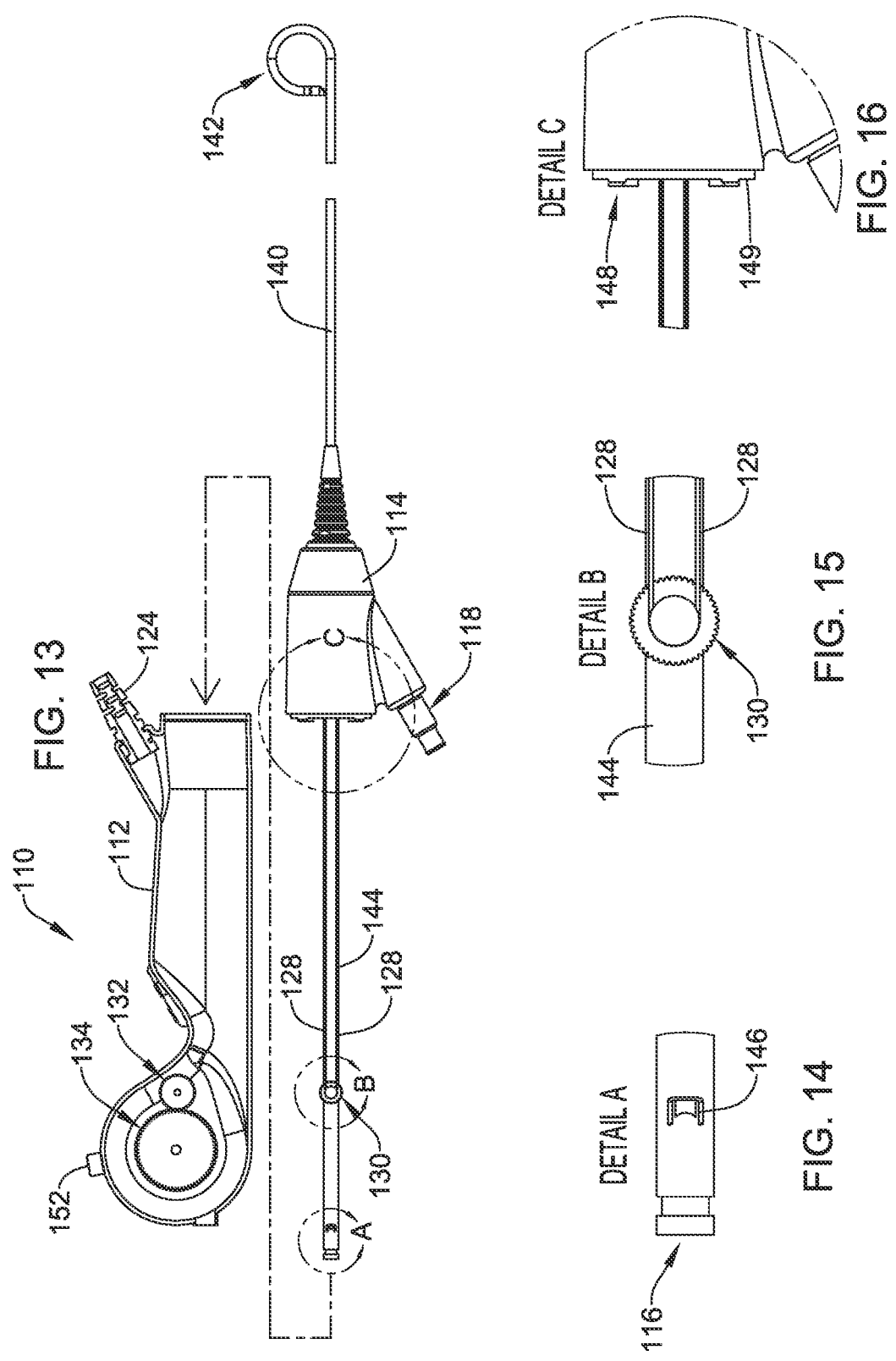
FIG. 13 illustrates one variation of components of the medical device in a disassembled state.
FIG. 14 is an enlarged view of Detail A of FIG. 13.
FIG. 15 is an enlarged view of Detail B of FIG. 13.
FIG. 16 is an enlarged view of Detail C of FIG. 13.
Figures 17, 18:
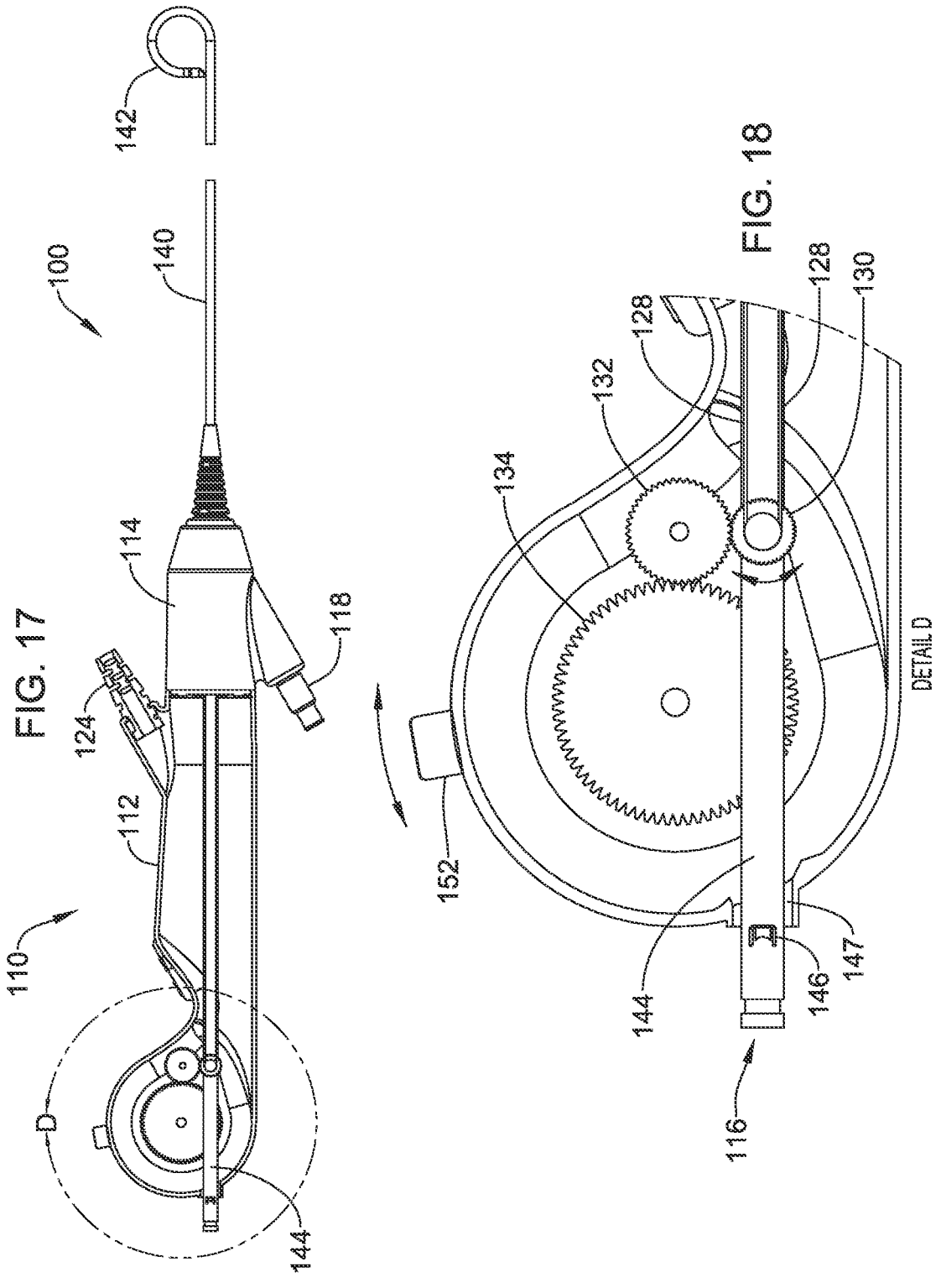
FIG. 17 illustrates the components of the medical device of FIG. 13 in an assembled state.
FIG. 18 is an enlarged view of Detail D of FIG. 17.

FIG. 13 illustrates one variation of the medical device 100 in a disassembled state and FIG. 17 illustrates this variation of the medical device in an assembled state. In the variation shown in FIG. 13, the proximal handle portion 112 may be coupled, such as releasably coupled, to the distal handle portion 114 and the elongate shaft 140 extending from the distal handle portion 114. In such instances, the proximal handle portion 112, including the electronics and/or optics connector 124 may be a reusable component of the medical device 100, whereas the distal handle portion 114 and the elongate shaft 140 may be a disposable component of the medical device 100. Therefore, the distal handle portion 114 and the elongate shaft 140 may be decoupled from the proximal handle portion 112, such as at the conclusion of a medical procedure or when desired to be exchanged for another distal handle portion 114 and elongate shaft 140 during a medical procedure, and a new distal handle portion 114 and elongate shaft 140 may be coupled to the proximal handle portion 112 for subsequent use during the medical procedure or a subsequent medical procedure, such as after sterilization of the proximal handle portion 112.

As shown in FIG. 13, the proximal portion 144 of the elongate shaft 140 may extend proximally of the distal handle portion 114 such that the proximal portion 144 is extendable into and/or through the proximal handle portion 112 As the distal handle portion 114 is being assembled with the proximal handle portion 112, the proximal end of the proximal portion 144 of the elongate shaft 140 may be guided into and/or through an opening 147 (see FIG. 18) in the proximal handle portion 112. In some instances, the opening 147 may include a flared region having a tapered or beveled surface to facilitate guiding the proximal end of the proximal portion 144 of the elongate shaft 140 into the opening 147.

The proximal portion 144 of the elongate shaft 140 may define the proximal port 116 in fluid communication with a working lumen extending through the elongate shaft 140 to the distal tip 142. Furthermore, the side port 118 may be provided with the distal handle portion 114, which may also be in fluid communication with the working lumen or an additional lumen extending through the elongate shaft 140 to the distal tip 142. In other embodiments, only the side port 118 is present and in fluid communication with the working lumen of the elongate shaft 140. In such instances, the proximal shaft 144 may be devoid of a lumen and provide support for components of the first actuation mechanism 150. In other embodiments, only the proximal port 116 is present and in fluid communication with the working lumen of the elongate shaft 140.

As shown in FIG. 14, in some embodiments, the proximal portion 144 of the elongate shaft 140 may include a proximal lock 146 configured to lock the elongate shaft 140 and/or the proximal portion 144 of the elongate shaft 140 axially relative to the handle 110 and/or the proximal handle portion 112 when the distal handle portion 114 is coupled to the proximal handle portion 112. For example, as shown in FIG. 17, when the distal handle portion 114 is fully coupled to the proximal handle portion 112, the proximal lock 146 may extend from and/or engage a proximal face of the proximal handle portion 112. For instance, the proximal lock 146 may include a deflectable tab, configured to engage the proximal face of the proximal handle portion 112 when the distal handle portion 114 is coupled to the proximal handle portion 112. Other locking mechanisms are also contemplated.

As shown in FIG. 16, in some instances the distal handle portion 114 may alternatively or additionally include a distal lock 148 configured to engage the proximal handle portion 112 when fully engaged therewith. For example, the distal handle portion 114 may include one or more, or a plurality of tabs configured to engage a mating locking structure (e.g., a slot, groove, etc.) of the proximal handle portion 114. In some instances, each tab may rotationally engage in a corresponding slot formed in the proximal handle portion 112. Thus, the tabs may be inserted longitudinally into the corresponding slots and then the distal handle portion 114 may be rotated relative to the proximal handle portion 112 until the tabs move into a locked position. Other locking mechanisms are also contemplated. The proximal face of the distal handle portion 114 may also include a lip 149 configured to fit into the proximal handle portion 112 when fully engaged therewith. The distal lock 148 is configured to rotationally lock the distal handle portion 114 relative to the proximal handle portion 112. However, in other embodiments, such as other variations described herein, the distal lock 148 may permit relative rotation of the distal handle portion 114 and elongate shaft 140 relative to the proximal handle portion 112.

The distal handle portion 114 may include an electrical interface, such as an electrical/data plug or connector configured to complete a detachable electrical connection with a mating electrical interface on the proximal handle portion 112 when fully coupled therewith. Accordingly, the mating electrical interfaces may electrically connect the electronics and/or optics connector 124 of the proximal handle portion 112 with the optics and/or illumination means extending through the elongate shaft 140 to the distal tip 142.

Details of the first actuation mechanism 150 will now be further described. The first actuation mechanism 150 may include a first gear 130, see FIG. 15, disposed along, over, on, and/or around the proximal portion 144 of the elongate shaft 140 and positionable within the proximal handle portion 112. The first gear 130 may be operably connected to the distal tip 142 of the elongate shaft 140 by one or more pull wires 128. Thus, the pull wires 128 may extend from the first gear 130 to the distal tip 142 and be secured thereto. In some embodiments, the first actuation mechanism 150 may include a second gear 132 disposed within the proximal handle portion 112 and operably connected to and/or configured to engage with the first gear 130 when the distal handle portion 114 is fully coupled to the proximal handle portion 112. A third, drive gear 134 may be operably connected to the first hinged arm 152 of the first actuation mechanism 150. However, in some embodiments, the second gear 132 may be operably connected to the first hinged arm 152 of the first actuation mechanism 150. It is understood that any desired arrangement and/or quantity of gears may be used as desired. In some embodiments, one or more additional gears may also be provided as means to change and/or adjust a gear ratio, torque transmission, or other factors between the first gear 130, the second gear 132, the third gear 134, and/or one or more additional gears. The second gear 132 may be engaged with the third, drive gear 134 such that rotation of the third, drive gear 134 causes counter rotation of the second gear 132. Thus, as shown in the detailed view of FIG. 18, manipulation of the first hinged arm 152 by the user results in rotation of the first gear 130 via corresponding rotation of the third, drive gear 134 and the second gear 132, and thus longitudinal actuation of the pull wires 128 to deflect the distal tip 142.

As illustrated in FIG. 18, the first gear 130 of the first actuation mechanism 150 may have a substantially circular cross-sectional shape, wherein a central axis of the first gear 130 is oriented substantially perpendicular to a central longitudinal axis of the proximal portion 144 of the elongate shaft 140. The first gear 130 may be rotatably secured to the proximal portion 144 of the elongate shaft 140. As such, the first gear 130 of the first actuation mechanism 150 may be configured to rotate relative to the proximal portion 144 of the elongate shaft 140 about the central axis of the first gear 130. The first gear 130 may be prevented from movement axially and/or longitudinally along the proximal portion 144 of the elongate shaft 140.

The first gear 130 of the first actuation mechanism 150 may include a first plurality of gear teeth extending around the first gear 130 of the first actuation mechanism 150. The second gear 132 of the first actuation mechanism 150 may include a second plurality of gear teeth extending around at least a portion of the second gear 132. The first plurality of gear teeth of the first gear 130 of the first actuation mechanism 150 may be configured to engage the second plurality of gear teeth of the second gear 132 of the first actuation mechanism 150.

In some instances, the proximal portion 144 of the elongate shaft 140 will deflect away from its longitudinal axis as the distal handle portion 114 is coupled to the proximal handle portion 112, to permit the first gear 130 to engage the second gear 132. The deflection of the proximal portion 144 of the elongate shaft 140 may generate a deflection force facilitating engagement of the gear teeth of the first gear 130 with the gear teeth of the second gear 132. The distal handle portion 114 and elongate shaft 140 may be non-rotatable relative to the proximal handle portion 112 to maintain engagement and alignment between the first plurality of gear teeth of the first gear 130 and the second plurality of gear teeth of the second gear 132.

The pull wires 128 may include a first wire having opposing ends secured to the distal tip 142 of the elongate shaft 140. The first wire may be wrapped around the first gear 130 to define a first portion extending from the pulley 136 to the distal tip 142 and a second portion extending from the pulley 136 to the distal tip 142. In an alternative configuration, proximal ends of the pull wires 128 may be secured to the first gear 130 of the first actuation mechanism 150 and distal ends of the pull wires 128 may be secured to the distal tip 142 of the elongate shaft 140.

As the first hinged arm 152 rotates counterclockwise (as viewed in FIG. 18), the first gear 130 may be rotated counterclockwise relative to the proximal portion 144 of the elongate shaft 140. In doing so, tension is applied to one of the pull wires 128 thereby deflecting the distal tip 142 in a first direction within a deflection plane that generally aligns with the side port 118 to provide a visual indication as to the orientation of the distal tip 142. Similarly, as the first hinged arm 152 rotates clockwise (as viewed in FIG. 18), the first gear 130 may be rotated clockwise relative to the proximal portion 144 of the elongate shaft 140. In doing so, tension is applied to the other pull wire 128 thereby deflecting the distal tip 142 in a second direction generally opposite the first direction within the deflection plane.

Figures 19, 20, 21, 22:
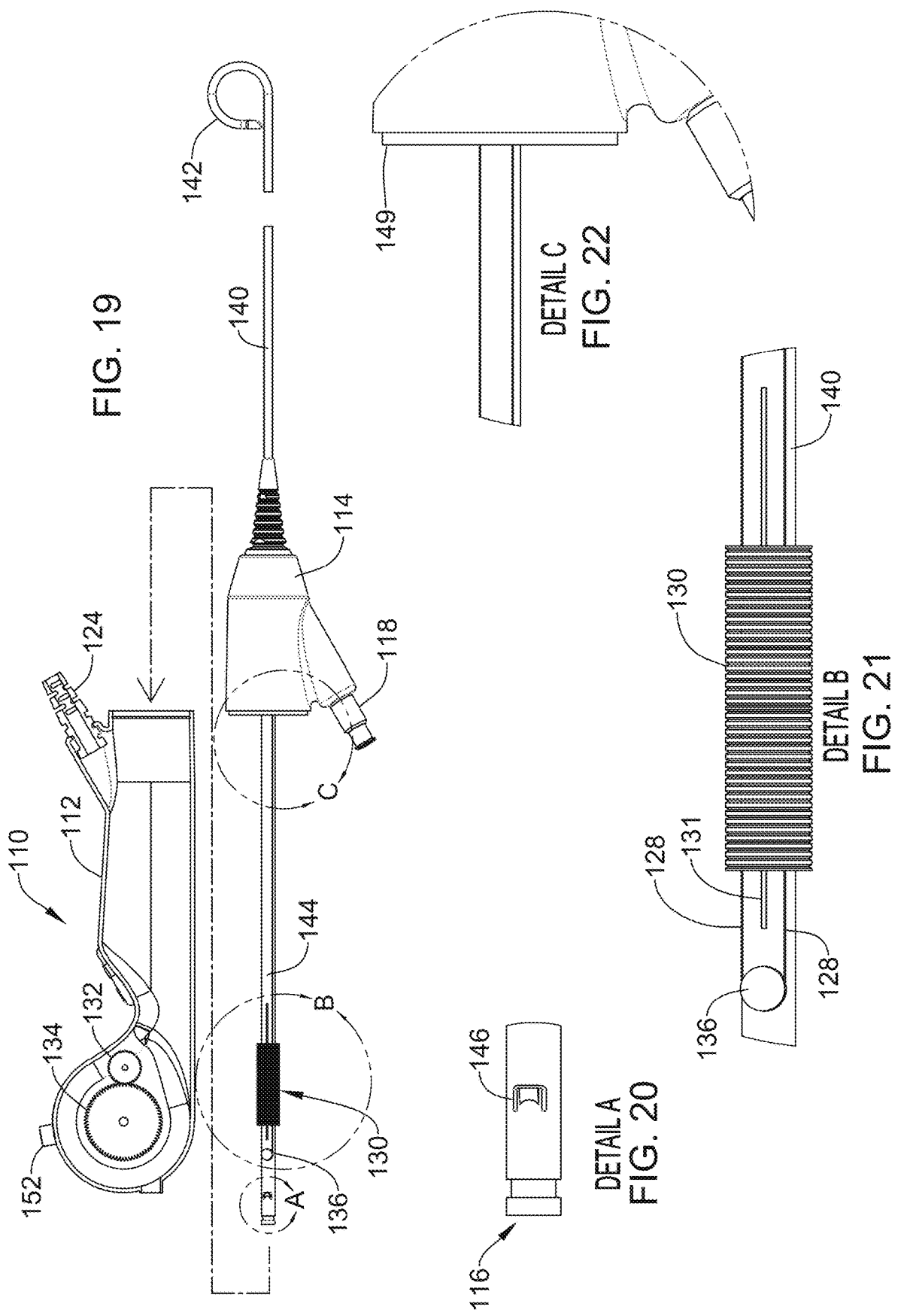
FIG. 19 illustrates another variation of components of the medical device in a disassembled state.
FIG. 20 is an enlarged view of Detail A of FIG. 19.
FIG. 21 is an enlarged view of Detail B of FIG. 19.
FIG. 22 is an enlarged view of Detail C of FIG. 19.
Figures 23, 24:
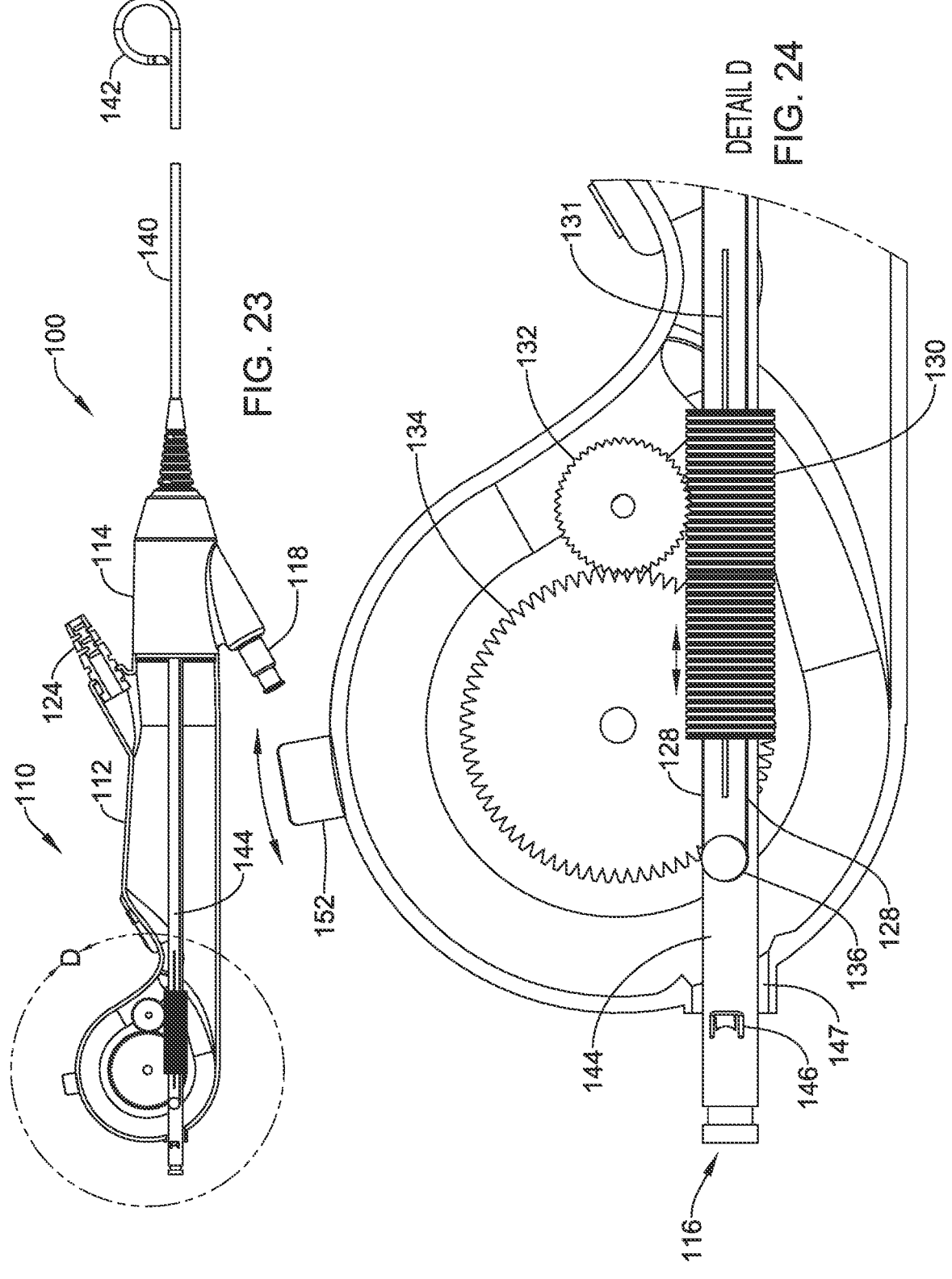
FIG. 23 illustrates the components of the medical device of FIG. 19 in an assembled state.
FIG. 24 is an enlarged view of Detail D of FIG. 23.

FIGS. 19-24 illustrate aspects of another variation of the medical device 100. This variation shares many features of the embodiment described in association with FIGS. 13-18. FIG. 19 illustrates the medical device 100 in a disassembled state and FIG. 23 illustrates this variation of the medical device in an assembled state. In the variation shown in FIG. 19, the proximal handle portion 112 may be coupled, such as releasably coupled, to the distal handle portion 114 and the elongate shaft 140 extending from the distal handle portion 114. In such instances, the proximal handle portion 112, including the electronics and/or optics connector 124 may be a reusable component of the medical device 100, whereas the distal handle portion 114 and the elongate shaft 140 may be a disposable component of the medical device 100. Therefore, the distal handle portion 114 and the elongate shaft 140 may be decoupled from the proximal handle portion 112 at the conclusion of a medical procedure or when desired to be exchanged for another distal handle portion 114 and elongate shaft 140 during a medical procedure, and a new distal handle portion 114 and elongate shaft

140 may be coupled to the proximal handle portion 112 for subsequent use during the medical procedure or a subsequent medical procedure, such as after sterilization of the proximal handle portion 112.

The elongate shaft 140 and/or the distal handle portion 114 may include a lock to couple the elongate shaft 140 and/or the distal handle portion 114 to the proximal handle portion 112. For instance, the proximal portion 144 of the elongate shaft 140 may include a proximal lock 146, shown in FIG. 20, configured to lock the elongate shaft 140 and/or the proximal portion 144 of the elongate shaft 140 axially relative to the handle 110 and/or the proximal handle portion 112 when the distal handle portion 114 is coupled to the proximal handle portion 112. For example, as shown in FIG. 24, when the distal handle portion 114 is fully coupled to the proximal handle portion 112, the proximal lock 146 may extend from and/or engage a proximal face of the proximal handle portion 112. For instance, the proximal lock 146 may include a deflectable tab, configured to engage the proximal face of the proximal handle portion 112 when the distal handle portion 114 is coupled to the proximal handle portion 112. Other locking mechanisms are also contemplated. The proximal lock 146 (e.g., the locking tab) may permit relative rotation between the elongate shaft 140 (and thus the distal handle portion 114) relative to the proximal handle portion 112, while preventing longitudinal movement therebetween.

In the variation of FIGS. 19-24, the distal handle portion 114 and elongate shaft 140 are configured to rotate relative to the proximal handle portion 112 when coupled thereto. For example, as shown in FIG. 24, when the distal handle portion 114 is fully coupled to the proximal handle portion 112, the proximal lock 146 may extend from and/or engage a proximal face of the proximal handle portion 112. For instance, the proximal lock 146 may include a deflectable tab, configured to engage the proximal face of the proximal handle portion 112 when the distal handle portion 114 is coupled to the proximal handle portion 112. Other locking mechanisms are also contemplated. Furthermore, as shown in FIG. 22, the proximal face of the distal handle portion 114 may also include a lip 149 configured to fit into the proximal handle portion 112 when fully engaged therewith. The lip 149 allows for rotational engagement between the distal handle portion 114 and the proximal handle portion 112 when the distal handle portion 114 is coupled to the proximal handle portion 112.

The distal handle portion 114 may include an electrical interface, such as an electrical/data plug or connector configured to complete a detachable electrical connection with a mating electrical interface on the proximal handle portion 112 when fully coupled therewith. Accordingly, the mating electrical interfaces may electrically connect the electronics and/or optics connector 124 of the proximal handle portion 112 with the optics and/or illumination means extending through the elongate shaft 140 to the distal tip 142.

The proximal portion 144 of the elongate shaft 140 may define the proximal port 116 in fluid communication with a working lumen extending through the elongate shaft 140 to the distal tip 142. Furthermore, the side port 118 may be provided with the distal handle portion 114, which may also be in fluid communication with the working lumen or an additional lumen extending through the elongate shaft 140 to the distal tip 142. In this variation, the proximal portion 144 of the elongate shaft, including the proximal port 116, as well as the side port 118 provided in the distal handle portion 114, may rotate relative to the proximal handle portion 112 when the elongate shaft 140 is rotated relative to the proximal handle portion 112 while rotatably coupled thereto.

In other embodiments, only the side port 118 is present and in fluid communication with the working lumen of the elongate shaft 140. In such instances, the proximal shaft 144 may be devoid of a lumen and provide support for components of the first actuation mechanism 150. In other embodiments, only the proximal port 116 is present and in fluid communication with the working lumen of the elongate shaft 140.

In this variation, the first actuation mechanism 150 may allow for the rotation of the distal handle portion 114 and elongate shaft 140 relative to the proximal handle portion 112. As illustrated in FIG. 21, the first gear 130 of the first actuation mechanism 150, which may be a worm gear, may have a substantially circular cross-sectional shape, wherein a central axis of the first gear 130 is oriented substantially parallel to a central longitudinal axis of the proximal portion 144 of the elongate shaft 140. In at least some embodiments, the central axis of the first gear 130 may be coaxial with the central longitudinal axis of the proximal portion 144 of the elongate shaft 140. In some embodiments, the first gear 130 of the first actuation mechanism 150 may be substantially cylindrical. The first gear 130 may include a central lumen extending axially therethrough. In some embodiments, the first gear 130 of the first actuation mechanism 150 may be slidably disposed along, over, on, and/or around the proximal portion 144 of the elongate shaft 140. In some embodiments, the proximal portion 144 of the elongate shaft 140 may extend axially through the central lumen of the first gear 130. As such, the first gear 130 of the first actuation mechanism 150 may be configured to move and/or slide relative to the proximal portion 144 of the elongate shaft 140 in an axial direction. In at least some embodiments, the proximal portion 144 of the elongate shaft 140 may include an axial rib 131 extending radially outward and configured to engage a corresponding recess (not shown) formed within the first gear 130, thereby preventing relative rotational movement between the first gear 130 and the proximal portion 144 of the elongate shaft 140. Other configurations for preventing relative rotational movement between the first gear 130 and the proximal portion 144 of the elongate shaft 140 (e.g., a set screw, a keying feature, a non-circular proximal portion 144, etc.) are also contemplated.

The first gear 130 of the first actuation mechanism 150 may include a first plurality of gear teeth extending along a length of the first gear 130 of the first actuation mechanism 150. Each tooth of the first plurality of gear teeth may extend circumferentially around the first gear 130 of the first actuation mechanism 150. The second gear 132 of the first actuation mechanism 150 may include a second plurality of gear teeth extending around at least a portion of the second gear 132. The first plurality of gear teeth of the first gear 130 of the first actuation mechanism 150 may be configured to engage the second plurality of gear teeth of the second gear 132 of the first actuation mechanism 150.

Proximal ends of the pull wires 128 may be secured to the first gear 130 of the first actuation mechanism 150 and distal ends of the pull wires 128 may be secured to the distal tip 142 of the elongate shaft 140. As shown in FIG. 21, the pull wires 128 include a first wire secured to and extending distally from a distal face of the first gear 130 to the distal tip 142 and a second wire secured to and extending proximally from a proximal face of the first gear 130 to a pulley 136, around the pulley 136, and then distally from the pulley 136, through a passage 131 formed in the first gear 130 and distally to the distal tip 142.

As shown in FIG. 24, as the first hinged arm 152 rotates counterclockwise, the first gear 130 may be axially translated along the proximal portion 144 of the elongate shaft 140 in a proximal direction. In doing so, tension is applied to the first wire of the one or more wires 128 thereby deflecting the distal tip 142 in a first direction within a deflection plane that generally aligns with the side port 118 to provide a visual indication as to the orientation of the distal tip 142. Similarly, as the first hinged arm 152 rotates clockwise (as viewed in FIG. 24), the first gear 130 may be axially translated along the proximal portion 144 of the elongate shaft 140 in a distal direction. In doing so, tension is applied to the second wire of the one or more wires 128 thereby deflecting the distal tip 142 in a second direction generally opposite the first direction within the deflection plane.

In this variation, the elongate shaft 140 may be fixedly attached to the distal handle portion 114 of the handle 110 yet rotatable relative to the proximal handle portion 112 of the handle 110. As such, the distal handle portion 114 may be rotatable relative to the proximal handle portion 112. The first plurality of gear teeth on the first gear 130 (e.g., worm gear) permits engagement with the second plurality of gear teeth of the second gear 132 regardless of the rotational orientation of the elongate shaft 140 relative to the proximal handle portion 112. The first gear 130 and the pulley 136 may be configured to be non-rotatable around the circumference of the elongate shaft 140. Accordingly, the first gear 130 and the pulley 136 may rotate within and relative to the proximal handle portion 112 as the elongate shaft 140 rotates relative to the proximal handle portion 112 so as to maintain the relative orientation of the one or more wires 128 with respect to the elongate shaft 140 and/or the distal tip 142 without twisting or entanglement of the one or more wires 128.

Figures 25, 26:
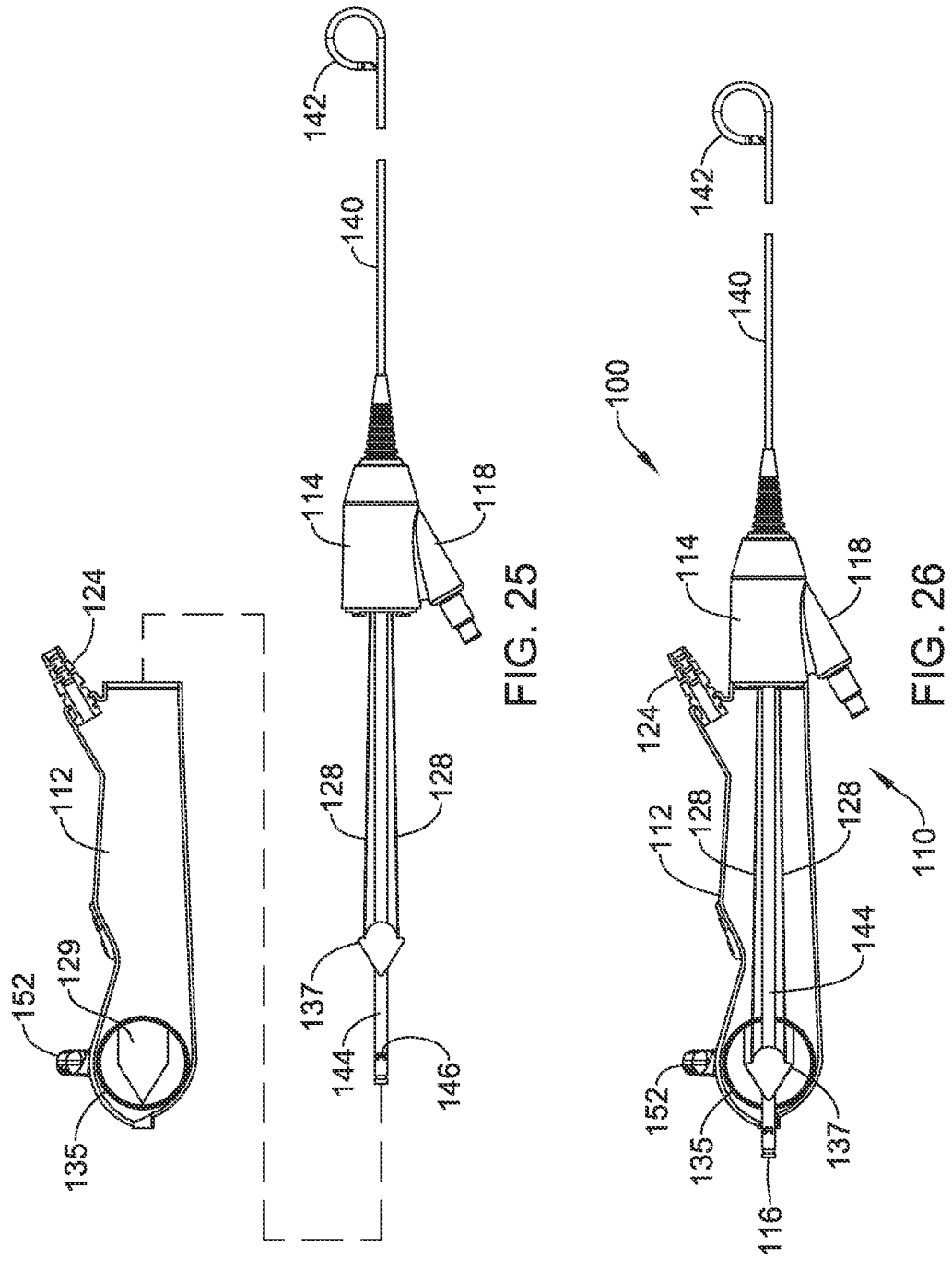
FIG. 25 illustrates another variation of components of the medical device in a disassembled state.
FIG. 26 illustrates the components of the medical device of FIG. 25 in an assembled state.

FIGS. 25 and 26 illustrate aspects of another variation of the medical device 100. This variation shares many features of the embodiment described in association with FIGS. 13-18. FIG. 25 illustrates the medical device 100 in a disassembled state and FIG. 26 illustrates this variation of the medical device in an assembled state. In the variation shown in FIGS. 25 and 26, the proximal handle portion 112 may be coupled, such as releasably coupled, to the distal handle portion 114 and the elongate shaft 140 extending from the distal handle portion 114. In such instances, the proximal handle portion 112, including the electronics and/or optics connector 124 may be a reusable component of the medical device 100, whereas the distal handle portion 114 and the elongate shaft 140 may be a disposable component of the medical device 100. Therefore, the distal handle portion 114 and the elongate shaft 140 may be decoupled from the proximal handle portion 112 at the conclusion of a medical procedure or when desired to be exchanged for another distal handle portion 114 and elongate shaft 140 during a medical procedure, and a new distal handle portion 114 and elongate shaft 140 may be coupled to the proximal handle portion 112 for subsequent use during the medical procedure or a subsequent medical procedure, such as after sterilization of the proximal handle portion 112.

The elongate shaft 140 and/or the distal handle portion 114 may include a lock to couple the elongate shaft 140 and/or the distal handle portion 114 to the proximal handle portion 112. For instance, the proximal portion 144 of the elongate shaft 140 may include a proximal lock 146, similar to that described above, configured to lock the elongate shaft 140 and/or the proximal portion 144 of the elongate shaft 140 axially relative to the handle 110 and/or the proximal handle portion 112 when the distal handle portion 114 is coupled to the proximal handle portion 112. For example, as shown in FIG. 26, when the distal handle portion 114 is fully coupled to the proximal handle portion 112, the proximal lock 146 may extend from and/or engage a proximal face of the proximal handle portion 112. For instance, the proximal lock 146 may include a deflectable tab, configured to engage the proximal face of the proximal handle portion 112 when the distal handle portion 114 is coupled to the proximal handle portion 112. In the variation of FIGS. 25 and 26, the distal handle portion 114 and elongate shaft 140 are configured to be rotationally fixed relative to the proximal handle portion 112 when coupled thereto. Other locking mechanisms are also contemplated.

Furthermore, similar to the features described above and illustrated in FIG. 16, the proximal face of the distal handle portion 114 may also include a distal lock configured to engage the proximal handle portion 112 when fully engaged therewith. For example, the distal handle portion 114 may include one or more, or a plurality of tabs configured to engage a mating locking structure (e.g., a slot, groove, etc.) of the proximal handle portion 114. In some instances, each tab may rotationally engage in a corresponding slot formed in the proximal handle portion 112. Thus, the tabs may be inserted longitudinally into the corresponding slots and then the distal handle portion 114 may be rotated relative to the proximal handle portion 112 until the tabs move into a locked position. Other locking mechanisms are also contemplated. The proximal face of the distal handle portion 114 may also include a lip configured to fit into the proximal handle portion 112 when fully engaged therewith. The distal lock is configured to rotationally lock the distal handle portion 114 relative to the proximal handle portion 112. However, in other embodiments, such as other variations described herein, the distal lock may permit relative rotation of the distal handle portion 114 and elongate shaft 140 relative to the proximal handle portion 112.

The proximal portion 144 of the elongate shaft 140 may define the proximal port 116 in fluid communication with a working lumen extending through the elongate shaft 140 to the distal tip 142. Furthermore, the side port 118 may be provided with the distal handle portion 114, which may also be in fluid communication with the working lumen or an additional lumen extending through the elongate shaft 140 to the distal tip 142. In other embodiments, only the side port 118 is present and in fluid communication with the working lumen of the elongate shaft 140. In such instances, the proximal shaft 144 may be devoid of a lumen and provide support for components of the first actuation mechanism 150. In other embodiments, only the proximal port 116 is present and in fluid communication with the working lumen of the elongate shaft 140.

Details of the first actuation mechanism 150 will now be further described. The first actuation mechanism 150 may include a first linkage member 137 disposed along, over, on and/or around the proximal portion 144 of the elongate shaft 140 and positionable within the proximal handle portion 112. The first linkage member 137 may be operably connected to the distal tip 142 of the elongate shaft 140 by one or more pull wires 128. Thus, the pull wires 128 may extend from the first linkage member 137 to the distal tip 142 and be secured thereto. The first linkage member 137 may rotate about a rotational axis extending perpendicular to the central longitudinal axis of the elongate shaft 140.

The first actuation mechanism 150 may include a second linkage member 135 disposed within the proximal handle portion 112 and operably connected to and/or configured to engage with the first linkage member 137 when the distal handle portion 114 is fully coupled to the proximal handle portion 112. For example, the second linkage member 135 may include a cavity or recess 129 configured to receive the first linkage member 137 therein when the distal handle portion 114 is fully engaged with the proximal handle portion 112. In the engaged configuration, an engagement surface of the first linkage member 137 may directly contact and be juxtaposed with an engagement surface of the second linkage member 135 such that forces can be transmitted between the first linkage member 137 and the second linkage member 135. Manipulation of the first hinged arm 152 by the user results in rotation of the linkage member 137 via corresponding rotation of the second linkage member 135, and thus longitudinal actuation of the pull wires 128 to deflect the distal tip 142.

Figure 27:
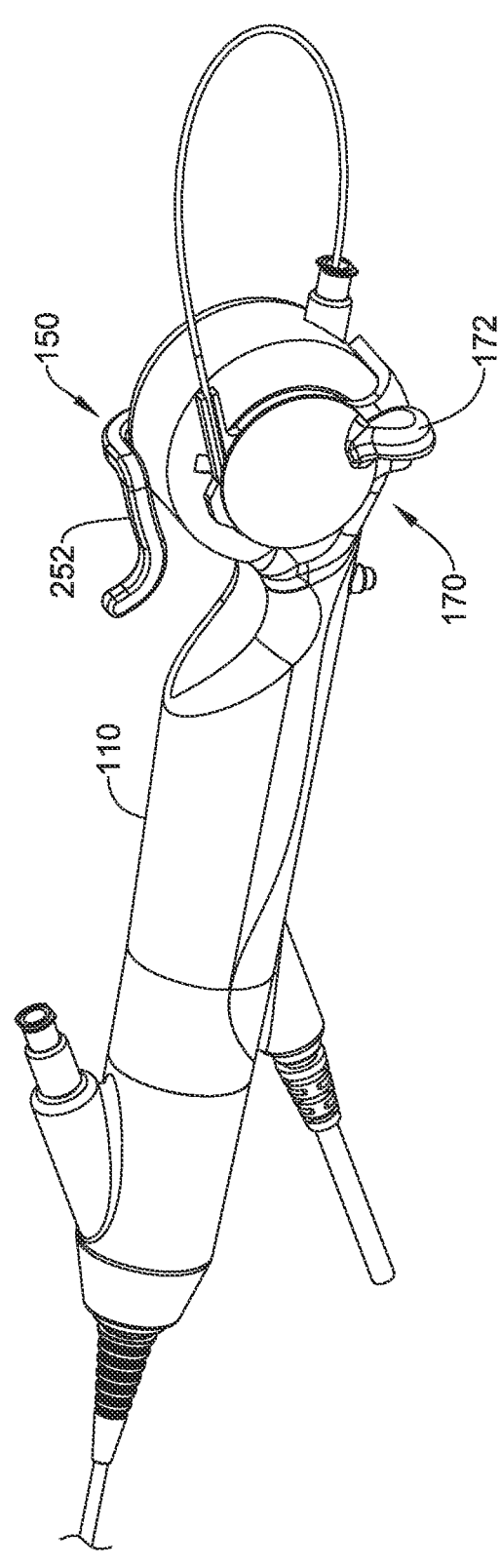
FIG. 27 illustrates an alternative configuration for the handle and actuation mechanisms of the medical device.

FIG. 27 illustrates an alternative configuration of the handle 110, the first actuation mechanism 150, and the second actuation mechanism 170. As will be appreciated, the shape, form, and/or configuration of some features may vary. In the illustrated configuration, the first actuation mechanism 150 may have the first hinged arm 152 configured to be actuated using the thumb 12 of the first hand 10 (e.g., FIG. 3) replaced with a first trigger arm 252 configured to be actuated using a finger of the first hand 10. This configuration still permits one handed operation and/or actuation of the handle 110, the first actuation mechanism 150, and the second actuation mechanism 170. It will be appreciated that in some alternative embodiments, the second hinged arm 172 of the second actuation mechanism 170, which is configured to be actuated using the thumb 12 of the first hand 10 (e.g., FIG. 3), may be replaced with a second trigger arm that is configured to be actuated using a finger of the first hand 10 instead of using the first trigger arm 252. In yet another alternative configuration, the first hinged arm 152 may be replaced with the first trigger arm 252 and the second hinged arm 172 may be replaced with the second trigger arm such that both the first actuation mechanism 150 and the second actuation mechanism 170 are actuatable using their respective trigger arms. Other configurations are also contemplated.

The first trigger arm 252 and/or the second trigger arm may be configured and/or may include many of the same features found on the first hinged arm 152 and/or the second hinged arm 172, respectively. For example, the first trigger arm 252 may include the first biasing element 158 configured as in the first hinged arm 152. In another example, the first trigger arm 252 may include the one or more projections 155 configured as in the first hinged arm 152. In another example, the first trigger arm 252 may include the first tooth 160 configured as in the first hinged arm 152. Similar construction and/or features may be applied to the second trigger arm with respect to the second hinged arm 172. In another example, the first trigger arm 252 and/or the second trigger arm may be self-locking as described herein with respect to the first hinged arm 152 and/or the second hinged arm 172, respectively. Other configurations are also contemplated.

The materials that can be used for the various components of the medical systems and the various elements thereof disclosed herein may include those commonly associated with medical system and/or devices. For simplicity purposes, the following discussion refers to the medical system. However, this is not intended to limit the devices and methods described herein, as the discussion may be applied to other elements, members, components, or devices disclosed herein, such as but not limited to the handle 110, the elongate shaft 140, the first actuation mechanism 150, the second actuation mechanism 170, the actuatable medical instrument 190, and/or elements or components thereof.

In some embodiments, the medical system and/or components thereof may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In some embodiments, a linear-elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a super-elastic nitinol can be used to achieve desired properties.

In at least some embodiments, portions or all of the medical system and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical system in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical system to achieve the same result.

In some embodiments, a degree of Magnetic Resonance Imaging (MRI) compatibility is imparted into the medical system and/or other elements disclosed herein. For example, the medical system and/or components or portions thereof may be made of a material that does not substantially distort the image and create substantial artifacts (i.e., gaps in the image). Certain ferromagnetic materials, for example, may not be suitable because they may create artifacts in an MRI image. The medical system or portions thereof may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the medical system and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the medical system and/or other elements disclosed herein may include and/or be formed from a textile material. Some examples of suitable textile materials may include synthetic yarns that may be flat, shaped, twisted, textured, pre-shrunk, or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum, or a Ni—Co—Cr-based alloy. The yarns may further include carbon, glass, or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun types. The type and denier of the yarn chosen may be selected in a manner which forms a biocompatible and implantable prosthesis and, more particularly, a vascular structure having desirable properties.

In some embodiments, the medical system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An endoscope configured to be actuated using a first hand of a user, comprising: a handle comprising a proximal handle portion and a distal handle portion; an elongate shaft extending distally from the distal handle portion; wherein the elongate shaft includes a distal tip that is deflectable using a first actuation mechanism secured to the proximal handle portion; wherein the handle includes a port in communication with the elongate shaft; and an actuatable medical instrument configured to be slidably disposed within the elongate shaft and the port; wherein a proximal end of the actuatable medical instrument is operably connected to a second actuation mechanism secured to the proximal handle portion; wherein the first actuation mechanism is configured to be actuated by a thumb of the first hand; wherein the second actuation mechanism is configured to be actuated by the thumb of the first hand; wherein the first actuation mechanism includes a first hinged arm, a first biasing element, and a first tooth integrally formed as part of the first hinged arm, the first tooth being configured to selectively engage and disengage a first plurality of teeth under direct user control; and wherein the second actuation mechanism includes a second hinged arm, a second biasing element, and a second tooth integrally formed as part of the second hinged arm, the second tooth being configured to selectively engage and disengage a second plurality of teeth formed in an actuation housing under direct user control, wherein the first hinged arm rotates around a first axis of rotation extending transversely through the proximal handle portion, and wherein the second hinged arm rotates around a second axis of rotation extending transversely through the proximal handle portion, wherein the first axis of rotation is coaxial with the second axis of rotation.

2. The endoscope of claim 1, wherein the first actuation mechanism is self-locking.

3. The endoscope of claim 1, wherein the first plurality of teeth are operably connected to the distal tip.

4. The endoscope of claim 3, wherein rotational movement of the first hinged arm by the thumb of the first hand causes the first plurality of teeth to axially translate along the elongate shaft;

wherein axial translation of the first plurality of teeth causes deflection of the distal tip.

5. The endoscope of claim 1, wherein the elongate shaft is rotatable relative to the proximal handle portion.

6. The endoscope of claim 1, wherein the actuation housing of the second actuation mechanism comprises a base portion and a cover portion configured to rotate relative to the base portion.

7. The endoscope of claim 6, wherein the second actuation mechanism is self-locking.

8. The endoscope of claim 6, wherein the actuatable medical instrument includes:

an outer sheath having an annular strain relief disposed about a proximal end of the outer sheath; and an inner wire slidably disposed within the outer sheath.

9. The endoscope of claim 8, wherein the annular strain relief is fixedly attached to the base portion of the actuation housing and the inner wire is attached to the cover portion.

10. The endoscope of claim 6, wherein the actuation housing is removably secured to proximal handle portion.

11. An endoscope configured to be actuated using a first hand of a user, comprising: a handle comprising a proximal handle portion and a distal handle portion extending along a central longitudinal axis; an elongate shaft extending distally from the distal handle portion; wherein the elongate shaft includes a distal tip that is deflectable using a first actuation mechanism secured to the proximal handle portion; wherein the handle includes a port in communication with a lumen extending through the elongate shaft; and an actuatable medical instrument configured to be slidably disposed within the lumen of the elongate shaft and the port; wherein a proximal end of the actuatable medical instrument is operably connected to the second actuation mechanism; wherein the first actuation mechanism is configured to be actuated by the first hand in a first position relative to the handle; wherein the first actuation mechanism includes a first hinged arm having a first free end and a first hinged end opposite the first free end, a first biasing element, and a first tooth integrally formed as part of the first hinged arm at the first end, the first tooth being configured to selectively engage and disengage a first plurality of teeth formed in the proximal handle portion under direct user control; wherein the first biasing element biases the first hinged arm toward a first locked position, wherein the first free end of the first hinged arm is biased away from the handle; a second actuation mechanism configured to be secured to the proximal handle portion; wherein the second actuation mechanism is configured to be actuated by the first hand in the first position relative to the handle; wherein the second actuation mechanism includes a second hinged arm having a second free end and a second hinged end opposite the second free end, a second biasing element, and a second tooth integrally formed as part of the second hinged arm at the second hinged end, the second tooth being configured to selectively engage and disengage a second plurality of teeth formed in an actuation housing under direct user control, wherein the first hinged arm rotates around a first axis of rotation extending transversely through the proximal handle portion substantially perpendicular to the longitudinal axis of the handle, and wherein the second hinged arm rotates around a second axis of rotation extending transversely through the proximal handle portion substantially perpendicular to the longitudinal axis of the handle, wherein the first axis of rotation is coaxial with the first axis of rotation.

12. The endoscope of claim 11, wherein the second biasing element biases the second hinged arm toward a second locked position, wherein the second free end of the second hinged arm is biased away from the handle.

13. The endoscope of claim 12, wherein the second actuation mechanism includes the actuation housing comprising a base portion and a cover portion configured to rotate relative to the base portion.

14. The endoscope of claim 11, wherein the proximal handle portion includes a deflection indicator disposed on an outside surface of the proximal handle portion;

wherein when the first hinged arm is moved away from a home position relative to the proximal handle portion the deflection indicator is visible.

15. The endoscope configured to be actuated using a first hand of a user, comprising: a handle comprising a proximal handle portion and a distal handle portion detachably couplable to the proximal handle portion; an elongate shaft having a distal portion extending distally from the distal handle portion and a proximal portion extending proximally from the distal handle portion into the proximal handle portion; a first actuation mechanism configured to deflect a distal tip of the elongate shaft for endoscopic visualization and navigation; wherein a first gear or linkage of the first actuation mechanism is coupled to the proximal portion of the elongate shaft and a second gear or linkage of the first actuation mechanism is coupled to the proximal handle portion; and wherein the first gear or linkage of the first actuation mechanism engages the second gear or linkage of the first actuation mechanism when the distal handle portion is coupled to the proximal handle portion; a second actuation mechanism configured to be secured to the proximal handle portion for actuating medical instruments; wherein a first gear or linkage of the second actuation mechanism is coupled to an actuation housing and a second gear or linkage of the second actuation mechanism is coupled to the proximal handle portion, wherein the first actuation mechanism includes a first hinged arm configured to rotate around a first axis of rotation extending transversely through the proximal handle portion, and wherein the second actuation mechanism includes a second hinged arm configured to rotate around a second axis of rotation extending transversely through the proximal handle portion, wherein the first axis of rotation is coaxial with the second axis of rotation.

16. The endoscope of claim 15, wherein the distal handle portion and the elongate shaft are rotatably coupled to the proximal handle portion.

17. The endoscope of claim 16, wherein the first gear or linkage of the first actuation mechanism is a worm gear longitudinally slidable along the proximal portion of the elongate shaft.

18. The endoscope of claim 17, further comprising a plurality of pull wires extending from the worm gear to the distal tip.

* * * * *